United States Patent
Martel et al.

(10) Patent No.: US 11,982,676 B2
(45) Date of Patent: May 14, 2024

(54) NEAR-INFRARED FLUORESCENT NANOPROBE

(71) Applicants: VALORISATION-RECHERCHE, LIMITED PARTNERSHIP, Quebec (CA); POLYVALOR, LIMITED PARTNERSHIP, Quebec (CA); CENTRE NATIONAL DE LA RECHERCHE SCIENTIFIQUE, Paris (FR)

(72) Inventors: Richard Martel, Montréal (CA); Étienne Gaufrès, Talence (FR); Charlotte Allard, Montréal (CA)

(73) Assignees: VALORISATION-RECHERCHE, LIMITED PARTNERSHIP, Quebec (CA); POLYVALOR, LIMITED PARTNERSHIP, Quebec (CA); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 145 days.

(21) Appl. No.: 17/232,419

(22) Filed: Apr. 16, 2021

(65) Prior Publication Data
US 2021/0325399 A1 Oct. 21, 2021

(51) Int. Cl.
*C09K 11/06* (2006.01)
*G01N 21/64* (2006.01)
*G01N 33/58* (2006.01)

(52) U.S. Cl.
CPC ....... *G01N 33/587* (2013.01); *G01N 21/6428* (2013.01); *G01N 21/6456* (2013.01);
(Continued)

(58) Field of Classification Search
CPC ..... C09K 11/06; G01N 33/587; G01N 33/586
See application file for complete search history.

(56) References Cited

U.S. PATENT DOCUMENTS 9,395,305 B2 7/2016 Martel et al.
10,209,194 B2 2/2019 Martel et al.
2021/0154335 A1* 5/2021 Johnston ............ A61K 49/0058

OTHER PUBLICATIONS

Lutsyk. Self-Assembly for Two Types of J-Aggregates: cis-Isomers of Dye on he Carbon Nanotube Surface and Free Aggregates of Dye translsomers. J. Pjhys. Chem. C 2019, 123, 19903-19911 (Year: 2019).*

(Continued)

*Primary Examiner* — Matthew E. Hoban
(74) *Attorney, Agent, or Firm* — Hovey Williams LLP; Crissa Crook

(57) ABSTRACT

A fluorescent probe having a capsule of nanometric size and an aggregate of fluorogenic molecules coupled to the capsule is provided. The aggregate emits a fluorescent signal at one or more wavelengths within the fluorescence spectral range when the probe is illuminated by an excitation light beam at one or more wavelengths within the excitation spectral range. Preferably, the fluorescent spectral range is in the near-infrared region of the spectrum. In some embodiments, the capsule is a boron nitride (BN) nanotube and the aggregate comprise 3,6-Bis[2,2']bithiophenyl-5-yl-2,5-di-n-octylpyrrolo[3,4-c]pyrrole-1,4-dione as fluorogenic molecules. In some embodiments, the 3,6-Bis[2,2']bithiophenyl-5-yl-2,5-di-n-octylpyrrolo[3,4-c]pyrrole-1,4-dione fluorogenic molecules are in a J-aggregation state.

18 Claims, 8 Drawing Sheets

(52) U.S. Cl.
CPC ............ *G01N 33/582* (2013.01); *C09K 11/06* (2013.01); *G01N 2021/6439* (2013.01)

(56) References Cited

OTHER PUBLICATIONS

Gaufrès, et al., "Aggregation Control of α-Sexithiophene via Isothermal Encapsulation Inside Single-Walled Carbon Nanotubes", ACS Nano, 2016, 10, pp. 10220-10226.
Ciofani, et al., "A simple approach to covalent functionalization of boron nitride nanotubes", J Colloid and Interface Sci., 2012, 374, pp. 308-314.
Gaufrès, et al., "Giant Raman scattering from J-aggregated dyes inside carbon nanotubes for multispectral imaging", Nature Photonics, 2014, 8, pp. 72-78.

Yao, et al., "FloDots: luminescent nanoparticles", Anal Bioanal Chem, 2006, 385, pp. 518-524.
Siciliano, et al., "How Daphnia (Cladocera) Assays may be used as Bioindicators of Health Effects?", J Biodivers Endanger Species, 2015, S1(5), 6 pages.
Welsher, et al., "A route to brightly fluorescent carbon nanotubes for near-infrared imaging in mice", Nature Nanotechnology, 2009, 4, pp. 773-780.
Hong, et al., "Near-infrared fluorophores for biomedical imaging", Nature Biomedical Engineering, 2017, 1(10), 22 pages.
Niskanen, et al., "Boron nitride nanotubes as vehicles for intracellular delivery of fluorescent drugs and probes", Nanomedicine, 2015, 17 pages.
Hong, et al., "Carbon Nanomaterials for Biological Imaging and Nanomedicinal Therapy", Chem Rev., 2015, 115, pp. 10816-10906.

* cited by examiner

NEAR-INFRARED FLUORESCENT NANOPROBE

CROSS-REFERENCE TO RELATED APPLICATIONS

The present application claims the priority benefit of Canadian Application Serial No. 3,078,133, filed Apr. 17, 2020, entitled NEAR-INFRARED FLUORESCENT NANOPROBE, incorporated by reference in its entirety herein.

TECHNICAL FIELD

The present description relates, generally, to the field of fluorescence spectroscopy and imaging and, more specifically, to the preparation and use of nanoscale probes for molecular fluorescence spectroscopy and imaging in the near-IR.

BACKGROUND

Current optical methods extensively use fluorescence probes to provide optical contrast in imaging and optical labeling. Fluorescence emission is often provided by fluorogenic dyes, which are used for applications such as lighting, pigments, analytical chemistry, forensics, civil security, data storage, etc. Fluorescence labelling is used in many different applications such as biological imaging, medical diagnosis, automated DNA sequencing, immunoassay, etc. Because of the interest to image deeper into large animals, which is provided by new imaging tools working in the NIR I and II optical bio-windows, there is a growing need to develop fluorescence probes that are active and bright in the NIR I and II spectral range.

Fluorescence probes are generally based on molecular dyes that are designed to provide light emission with high quantum yield and good wavelength tunability from the near infrared (NIR) to the ultraviolet (UV) regions of the spectrum. The emission characteristics of dyes present, however, limitations related to wavelength range as they are generally limited to the visible, photobleaching, chemical reactivity, blinking effects, and lifetime issues due to intersystem energy crossings, triplet annihilation, energy transfer, etc. These limitations are detrimental for applications because they lead to abnormally low brightness (number of photons emitted per photons absorbed) or unstable fluorescence emission (changes in brightness per time unit) or sudden energy shifts and intensity fluctuation of the emission spectrum. Other qualities looked for in fluorogenic probes are resistance to degradation (e.g. due to oxidative harsh environments) and to photobleaching, high stability as light sources (i.e. the light emission does not change in time), quantitativity (e.g. signal proportional to concentration) and no or low sensitivity to environmental effects.

A known solution to the photobleaching issues with dyes is the use of oxygen blocking molecules, such as anoxia, which effect is to significantly reduce photooxidation and parasitic reactions between ambient oxygen and the fluorogenic dyes. An alternative solution to the low or instable fluorescence emission consists of encapsulating or isolating dye molecules from the environment (oxygen, quenchers) using porous materials, such as mesoporous silica or using large supramolecular assemblies, such as rotaxane, cucurbiturils (cyclodextrine analogue) and so forth. It was shown, for instance, that instabilities and quenching of fluorescence is eliminated by embedding fluorogenic dyes in a polymer host, such as polysaccharide, PMMA, PPV and PFO, or cyclodextrin rings. The encapsulation of the dyes in inorganic materials, such as silica and calcium phosphate nanoparticles, is also reported to enhance the photostability and luminescent yield and probes as small as 7-10 nm in diameter have been synthesized for bioapplications [G. Yao, L. Wang, Y. Wu, J. Smith, J. Xu, W. Zhao, E. Lee and W. Tan, *FloDots: luminescent nanoparticles*, Anal Bioanal Chem (2006) 385: 518-524]. While these solutions can reduce or eliminate decreasing fluorescence brightness and energy transfer issues, the protection from inorganic materials is limited due to the poor dielectric quality of the host and the presence of quenching defects. Protection against quenchers from organic materials is not complete or stable structurally and does not completely stop molecular diffusion.

The encapsulation of various fluorescent dyes in highly crystalline nanomaterials, such as carbon nanotubes, has been explored and there are few reports of fluorescence emission from these assemblies. However, it was recently demonstrated that the fluorescence is efficiently quenched by the carbon nanotube. The small bandgap of the material and its physical proximity to the active dyes provides a highly efficient channel for quenching, giving no or only poor fluorescence emission signals from the assembly [E. Gaufrès, N. Y-W. Tang, A. Favron, C. Allard, F. Lapointe, V. Jourdain, S. Tahir, C. N. Brosseau, R. Leonelli and R. Martel, Aggregation Control of α-Sexithiophene Via Isothermal Encapsulation Inside Single-Walled Carbon Nanotubes, ACS Nano 10, 10220-10226 (2016)]. Taking advantage of this active quenching, it was shown that the dyes-carbon nanotube assembly system is well adapted for making Raman nanoprobes [R. Martel, M. A. Nadon, N. Y.-W. Tang, J. Cabana et J.-F. Raymond, RAMAN SCATTERING NANOPROBES U.S. Pat. No. 9,395,305 (Jul. 19, 2016); E. Gaufrès, N. Y. W. Tang, F. Lapointe, J. Cabana, M. A. Nadon, F. Raymond, T. Szkopek and R. Martel, *Giant Raman Scattering from J-Aggregated Dyes inside Carbon Nanotubes for Multispectral Imaging*, Nature Photonics 8, 72-78 (2014)]. Recent experiments performed by the inventors and independently in the group of F. Winnik [Niskanen, J. et al. Boron nitride nanotubes as vehicles for intracellular delivery of fluorescent drugs and probes. *Nanomedicine* 11, 5, 447-463 (2016)] have shown that an isolation of fluorescence dyes into highly crystalline and wide-bandgap materials does not quench luminescence as it is the case with carbon nanotubes. The simple and cost-effective methods of encapsulation should therefore help stabilizing dyes and the wide band-gap inorganic materials should act as a transparent window for fluorescence emission. Hence, it is expected that the encapsulation of molecules into inorganic nanotubes, e.g. ZnO, MgO and BN nanotubes, is effective in protecting the fluorescent properties of the dyes.

As already demonstrated with BN nanotubes (BNNT), a variety of different functionalization chemical groups may be used at the surface to help dispersion in water. The functionalization chemical group may involve pegylation or reaction with glycine. The functionalization chemical group acts as a dispersive chemical group that facilitates the dispersion and limit aggregation of BNNTs in a liquid. The functionalization chemical group may have a generic chemical functionalization which allows bonding with secondary chemical groups capable of bonding with the target material, which has been studied with BNNT in the context of drug delivery.

SUMMARY

In accordance with one aspect, there is provided a fluorescent probe comprising a capsule of nanometric size and an aggregate of fluorogenic molecules coupled to the capsule. The aggregate emits a fluorescent signal at one or more wavelengths within the fluorescence spectral range when the probe is illuminated by an excitation light beam at one or more wavelengths within the excitation spectral range. Preferably, the fluorescent spectral range is in the near-infrared region of the spectrum.

In some embodiments, the capsule is a boron nitride (BN) nanotube and the aggregate comprise 3,6-Bis[2,2']bithiophenyl-5-yl-2,5-di-n-octylpyrrolo[3,4-c]pyrrole-1,4-dione as fluorogenic molecules. In some embodiments, the 3,6-Bis[2,2]bithiophenyl-5-yl-2,5-di-n-octylpyrrolo[3,4-c]pyrrole-1,4-dione fluorogenic molecules are in a J-aggregation state.

In one implementation, the fluorescent spectral range of the aggregate of fluorogenic molecules is shifted and/or broadened from the visible range for the molecules in a free state, to the NIR1 and NIR2 range when encapsulated in aggregate form. In some implementations, the spectral shift of the fluorescent emission range is of the order of 600 nm.

In accordance with other aspects, there are provided a method for manufacturing a probe as above and a fluorescent investigation.

Other features and advantages of the invention will be better understood upon reading of preferred embodiments thereof with reference to the appended drawings.

DETAILED DESCRIPTION

Figure 1:
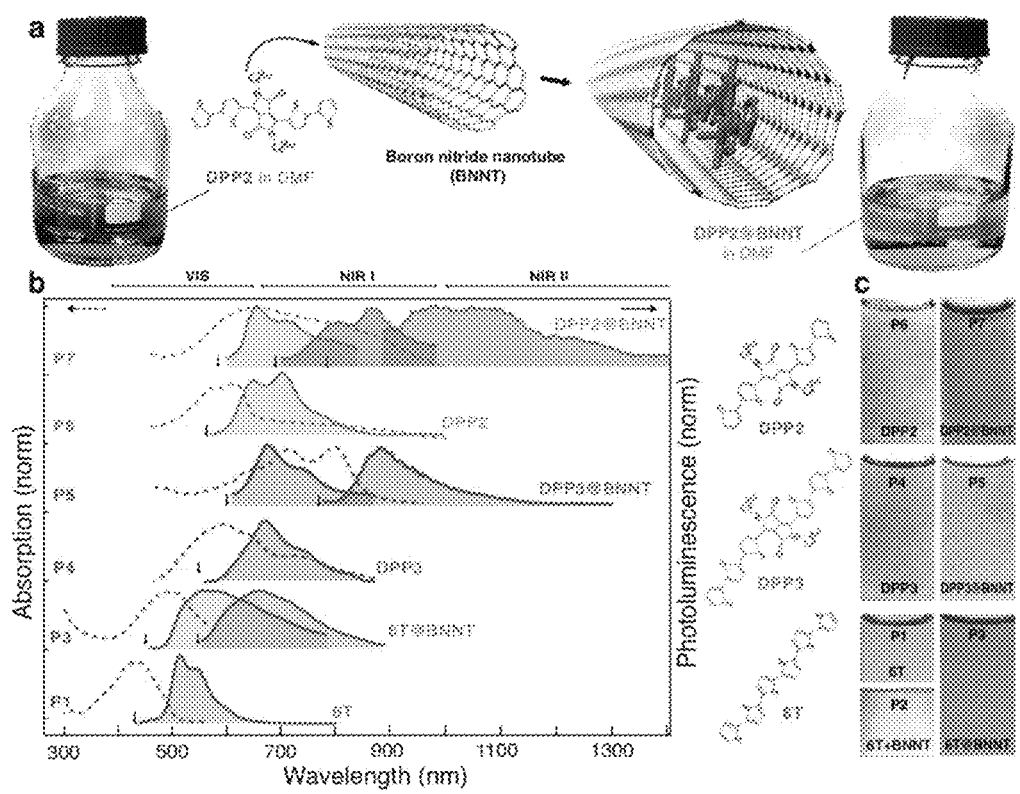
FIG. 1: Absorption and fluorescence properties of 6T@BNNTs, DPP2@BNNTs and DPP3@BNNTs. a, Schematic view of the encapsulation of DPP2 dye in a double-wall BNNT and the resulting colour change before and after encapsulation in DMF. b, Absorption (dashed) and fluorescence (continuous) spectra at room temperature of the solutions P1 and P3-P7. The excitation wavelength used for each PL spectrum is indicated by a vertical black arrow. c, Schematics of 6T and DPP-based dyes molecules (left) and pictures of the solutions in DMF before and after a liquid phase (toluene) encapsulation at different temperatures: 25° C. (P2) and 115° C. (P3) for 6T; 80° C. for DPPs (P5 and P7). P1, P4 and P6 are solutions of free dyes (no BNNT) in DMF.

In accordance with one aspect, there is provided a fluorescent probe.

Fluorescent probes such as described herein may be used in a variety of fluorescent imaging applications. Some non-limitative examples include in vivo imaging, vascular bioimaging, immunoassay, diagnosis, in-vivo labeling, tagging, selective targeting, etc.

Fluorescence is understood as a type of luminescence characterised by the emission of light at a fluorescent wavelength from molecules having absorbed light at an excitation wavelength different than the excitation wavelength. The expression fluorophore is understood to refer to a chemical compound emitting fluorescent light upon excitation. The expression fluorogenic is understood to refer to the capability to emit light under photoexcitation.

In some implementations, the fluorescent probes described herein emit fluorescent light in the Near InfraRed (NIR) range upon excitation by visible light. In some embodiments, the fluorescent probes emit in the NIR1 range, for example encompassing wavelengths from 750 nm to 1000 nm as defined by Hong G., Diao S., Antaris A. L., and Dai H., Carbon Nanomaterials for Biological Imaging and Nanomedicinal Therapy (2015), Chem. Rev. 115, 10816-1090. In other embodiments, the fluorescent probes emit in the NIR2 range, for example encompassing wavelengths from 1000 nm to 1700 nm as defined by Hong, G., Antaris, A. L., and Dai, H. (2017). Near-infrared fluorophores for biomedical imaging. Nature Biomedical Engineering, 2017, 1(1), 1-22. The spectral range within which the fluorescent probe emit fluorescent light may be referred to herein below as the fluorescence spectral range, whereas the spectral range encompassing the excitation wavelength or wavelengths may be referred to as the excitation spectral range.

In accordance with one aspect, the fluorescent probe includes a capsule of nanometric size and an aggregate of fluorogenic molecules coupled to the capsule. The aggregate emits a fluorescent signal at one or more wavelengths within the fluorescence spectral range when the probe is illuminated by an excitation light beam at one or more wavelengths within the excitation spectral range.

In some embodiments, the capsule is a boron nitride nanotube. Such capsules may be referred herein as BNNTs. Advantageously, boron nitride nanotubes are transparent over a large portion of the electromagnetic spectrum, including ultraviolet light, visible light and IR light. In some variants, the boron nitride nanotubes can include single-walled BNNTs or multi-walled BNNTs such as double-walled BNNTs. In some implementations, the BNNTs may have outer diameters between 1 nm and 15 nm. In some other implementations, the outer diameters of the BNNTs can be between 1 and 10 nm. For instance, the BNNTs' outer diameters can be between 2 nm and 10 nm, or between 2 nm and 5 nm or between 1 nm and 3 nm. In some implementations, the BNNTs may have inner diameters of 9 nm or less. For instance, the BNNTs inner diameters can be in the range between 0.7 nm and 9 nm, or between 1 nm and 9 nm. In some implementations, the BNNTs' inner diameters can be between 1 nm and 7 nm, or between 0.9 nm and 2 nm or between 0.7 nm and 1.5 nm. It will however be readily understood that capsules of different shapes and/or compositions may also be used, provided that the capsule is sufficiently transparent over the excitation spectral range and fluorescence spectral range of the probe. In some variants, the capsule may for example be embodied by other inorganic (e.g. BN, ZnO, SiOx, TiOx, Vox, CrxOy, AgxS, FexOy, MnxOy, etc.) or hybrid organic-inorganic (e.g. polymer-SiOx, lipids-ZnO, polymer-ZnO, etc.) nanostructures, such as boron nitride nanosheet assemblies with cavities, hollow nanospheres, hollow nanocones, hollow shell, etc.

In some implementations, the fluorescent probe may include multiple capsules bundled together. The multiple capsules may all be of a same shape and composition or include sets of capsules of different types. In some implementations, the number of capsules bundled together for one probe can be of the order of 5 or less or of 10 or less or of 50 or less.

As mentioned above, the nanoprobe further includes an aggregate of fluorogenic molecules coupled to the capsule.

In some implementations, the fluorogenic molecules may be embodied by a small dye molecule such as an oligothiophene derivative. In some embodiments, the fluorogenic molecules can include α-sexithiophene (also referred to as "6T" in the present description) or an oligothiophene containing a diketopyrrolopyrrole (DPP) core. In some embodiments, the oligothiophene containing a diketopyrrolopyrrole (DPP) core can have the following formula (I) or (II)

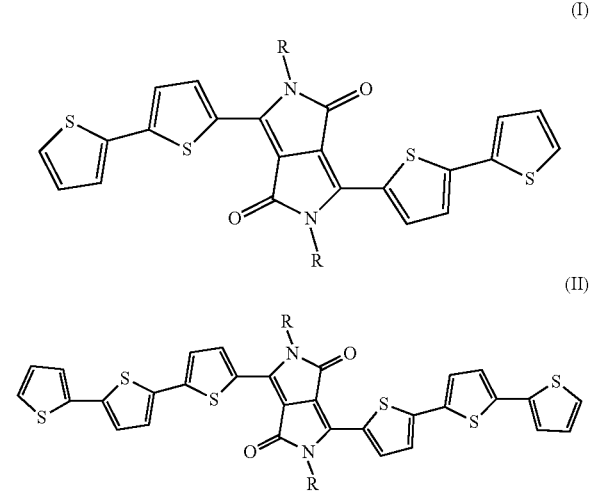

wherein R, independently of one another, can represent hydrogen, a branched or unbranched alkyl group having from 1 to 20 carbon atoms, a short (e.g., 1 to 12 units) polyethylene glycol (PEG) group, a butyloxycarbonyl (Boc)

group or ter-Boc group, or a combination of any of these groups or of other similar terminal groups. In some embodiments, the compound of formula (I) or (II) is such that R represents a branched or unbranched alkyl group having 8 carbon atoms. Preferably, R represents a group n-octyl. Hence, in some embodiments, the fluorogenic molecule can include a compound of formula (I) where R is n-octyl and the compound is 3,6-Bis[2,2']bithiophenyl-5-yl-2,5-di-n-octylpyrrolo[3,4-c]pyrrole-1,4-dione also referred to as "DPP2". In other embodiments, the fluorogenic molecule can include a compound of formula (II) where R is n-octyl and the compound is referred to as "DPP3".

The expression "aggregate" is understood to refer to an assembly of fluorogenic molecules, which is coupled to the capsule. The assembly of fluorogenic molecules can have a certain cohesion, which can result from an ordering of the molecules due to intermolecular interaction. In some embodiments, the aggregate can include substantially aligned individual fluorogenic molecules. In some embodiments, the aggregate can be present inside the BNNT's capsule. Depending on the inner diameter of the BNNT, both complex or simple alignments can be formed, which can lead to a mixture of aggregation states. In some embodiments, the aggregate can include fluorogenic molecules that are stacked in a head-to-tail arrangement. This arrangement is also referred to as "J-aggregation state" and can be explained by a dipolar interaction between the fluorogenic molecules. In some embodiments, the aggregate can include fluorogenic molecules in a face-to-face arrangement, also called side-by-side stacking. This latter arrangement is referred to as "H-aggregation state" and can be explained by a pi-pi stacking of the fluorogenic molecules. In some embodiments, an aggregate can include molecules in both J-aggregation state and H-aggregation state and can be explained by a mixture of dipolar interaction and pi-pi stacking between the fluorogenic molecules.

In some implementations, the aggregates of fluorescent molecules may be encapsulated within the capsule or, in an alternative embodiment, may be attached to the external surface thereof. In some variants, the probe may include one or more functionalization with chemical groups that are attached to an exterior of the capsule and that enable the connection between the capsule and a target material, and the aggregate of fluorescent molecules may be attached to of these functionalization chemical groups. Multiple aggregates of the same or of different fluorescent molecules may be both within the capsule and attached to the capsule exterior. They may be different from one another such that each contributes a different fluorescent emission when the probe is illuminated by an appropriate excitation light beam.

As mentioned above, the aggregate of fluorogenic molecules emits a fluorescent signal at one or more wavelengths within the fluorescence spectral range when the probe is illuminated by an excitation light beam at one or more wavelengths within the excitation spectral range. In accordance with one aspect, the coupling of the aggregate of fluorogenic molecules with the capsule transforms its light absorption and/or emission properties such that they are spectrally shifted and/or broadened and/or developed with additional red-shifted peaks (e.g. vibronic structures) compared to the same molecules in a free state.

In one implementation, the fluorescent emission range of the aggregate of fluorogenic molecules is shifted from the visible range for the molecules in a free state, to the NIR2 range when encapsulated in aggregate form. In some implementations, the spectral shift of the fluorescent emission range is of the order of 600 nm.

In accordance with one exemplary implementation, there is provided a fluorescent probe comprising a boron nitride nanotube in which is encapsulated an aggregate of 3,6-Bis [2,2]bithiophenyl-5-yl-2,5-di-n-octylpyrrolo[3,4-c]pyrrole-1,4-dione fluorogenic molecules, wherein the molecules are in a J-aggregation state. The probe emits fluorescent light having a spectral content with a fluorescent spectral range of (700-1300 nm) when excited by excitation light having a spectral content within an excitation spectral range of (530-800 nm).

Fabrication Method

The present description also concerns a method of preparing a fluorescent probe as described above.

In some implementations, the method includes providing a capsule of nanometric size such as a boron nitride nanotube. If not previously prepared, the method may also include a first step of cleaning and opening of the unprocessed nanometric capsule. Fluorogenic molecules are then coupled to the capsule, being either encapsulated within the capsule or attached to an exterior of the capsule. Attachment to the capsule exterior may be either by attachment directly to an external surface of the capsule or by attachment to a functionalization chemical group attached to the capsule external surface. Preparation of the capsule also includes attachment of a desired functionalization chemical group to the capsule external surface. The attached functionalization chemical group may bond indirectly, directly or selectively to a target material or host, or it may be a generic functionalization chemical group that bonds with any of a plurality of secondary chemical groups each of which bonds directly with a different predetermined target material. The functionalization step may precede or follow the introduction of the aggregate of fluorescent molecules.

Fluorescent Investigation Method

In another aspect, a probe as described herein may be used for performing a fluorescent investigation of a sample.

In some implementations, a fluorescent probe, as described above, is attached to a target material of interest within the sample, the fluorescent probe comprising a capsule of nanometric size to which is coupled at least one active aggregate of fluorescent molecules. The probe is attached to the target material via at least one functionalization chemical group that is attached to an exterior of the capsule and that forms a bond with the target material. The method further includes illuminating the sample with an excitation light beam having a wavelength that causes a fluorescence emission from the aggregate of fluorescent molecules, and detecting light resulting from the fluorescence, using an appropriate detector. The investigation may be a fluorescence imaging, lighting or lasing effect, or fluorescence or phosphorescence spectroscopic applications.

The invention and its advantages will become more apparent from the detailed description and examples that follow, which describe the various embodiments of the invention.

EXAMPLES

The sections below provide examples of results related to embodiments of fluorescent probes such as described above, and should not be taken as limitative to the scope of protection.

Herein, we report results on the preparation and on the chemical and fluorescence properties of dyes encapsulated inside BNNTs (dyes@BNNTs). Our experiments on α-sexithiophene (6T) and derivatives of 3,6-Bis[2,2]bithiophenyl-5-yl-2,5-di-n-octylpyrrolo[3,4-c]pyrrole-1,4-dione (DPP) encapsulated inside small diameter BNNTs ($d_{inner}$<3 nm) show a drastic improvement of the photostability compared to free dyes against laser light exposure. We observe strong absorption and emission bands from three different encapsulated dyes, red shifted in some cases by more than 600 nm compared to "free" (unencapsulated) dyes. We also report on effective passivation of the dyes against the environment, including harsh chemical conditions. Using various imaging demonstrations with living organisms (*Daphnia pulex*) and human cells (HuH6), we observe a reduced toxicity of the encapsulated dyes compared to free dyes and demonstrate their exceptional photostability as a nanoprobe for multimodal imaging in a wide range of wavelengths, including two-photons and single nanoprobe tracking.

FIG. 1 schematizes the main synthesis steps of the dye nanohybrids along with the absorption and fluorescence responses obtained before and after the encapsulation step. The synthesis begins by cutting raw BNNTs (BNNT LLC supplier) using mechanical grinding and ultrasound treatments. The resulting material is then purified in nitric acid and annealed at high temperature in air to suppress photoluminescence background from BN defects and $B_xO_y$ impurities (Supplementary FIG. 1). The last step is a liquid phase encapsulation of a selected dye molecule, e.g. DPP2 (FIG. 1a), in thus processed BNNTs, followed by a thorough rinsing in DMF/Toluene and finally with a piranha solution at room temperature to remove excess of dye molecules. The resulting solid residue can be dispersed in a solvent and yields a highly coloured solution, such as shown in FIG. 1a and c.

The first signature of encapsulation is a clear colour change compared to that of free dyes. In FIG. 1c, the coloration of the free 6T in DMF (P1) is compared to that of a mixture of 6T and BNNTs after an encapsulation step in toluene for 24 hours at 25° C. (P2) and 115° C. (P3). No change is observed between P1 and P2, whereas a clear change from yellow to red is observed for P3. As detailed below, the change in colour is driven by temperature and unambiguously indicates that the dyes have filled the BNNTs. Similar spectral changes of the dye resonances are also observed with other rod-like molecules. For example, the derivatives of 3,6-Bis[2,2']bithiophenyl-5-yl-2,5-di-n-oc-tylpyrrolo[3,4-c]pyrrole-1,4-dione (DPP2 and DPP3) are encapsulated using the same protocol but at 80° C. (FIG. 1c and Supplementary Section 2.2). The behaviour observed here with BNNTs is fully consistent with previous results from our group on dye encapsulation in SWCNTs [Gaufrès, E. et al. Aggregation control of α-Sexithiophene via isothermal encapsulation inside single-walled carbon nanotubes. *ACS Nano* 10, 10220-10226 (2016)]. For both types of nanotubes, the filling process is found to be endothermic, which is ascribed to a heat unbalance from intermolecular interactions between dyes (encapsulated) molecules and between (free) dyes and solvent molecules.

In FIGS. 1b, we explore more quantitatively the transformation using a comparison of different Dyes@BNNTs (P3, P5 and P7) in DMF with solutions of the same dyes in DMF (P1, P4, P6). The solutions of free dyes, namely 6T (P1), DPP3 (P4) and DPP2 (P6), displays absorption (dashed line) and fluorescence (continuous line) spectra characterized by vibronic band progressions that are typical for the dyes in DMF. Note that the concentration used for the solutions of free dyes have been adjusted to minimize self-aggregation in solution, which can significantly modify the vibronic progression. Surprisingly, the solutions of encapsulated dye molecules (P3-P5-P7) display drastically modified spectra and more complex vibronic structures. DPP3@BNNT and DPP2@BNNT present remarkable changes, such as new absorption and emissions bands that are significantly red shifted compared to that of free dyes. Interestingly, photo-excitation experiments on P5 and P7 solutions at energies within the absorption bands produce very distinct PL spectra, typically characterized by a broadened vibronic progressions and new emission bands significantly red-shifted compared to free dyes. For example, DPP2@BNNT excited at 690 nm and 800 nm show emission bands that are clearly shifted at around 900 nm and 1050-1200 nm, respectively. A similar behaviour, although not as drastic, is seen with 6T@BNNT solutions (P3).

Figure 2:
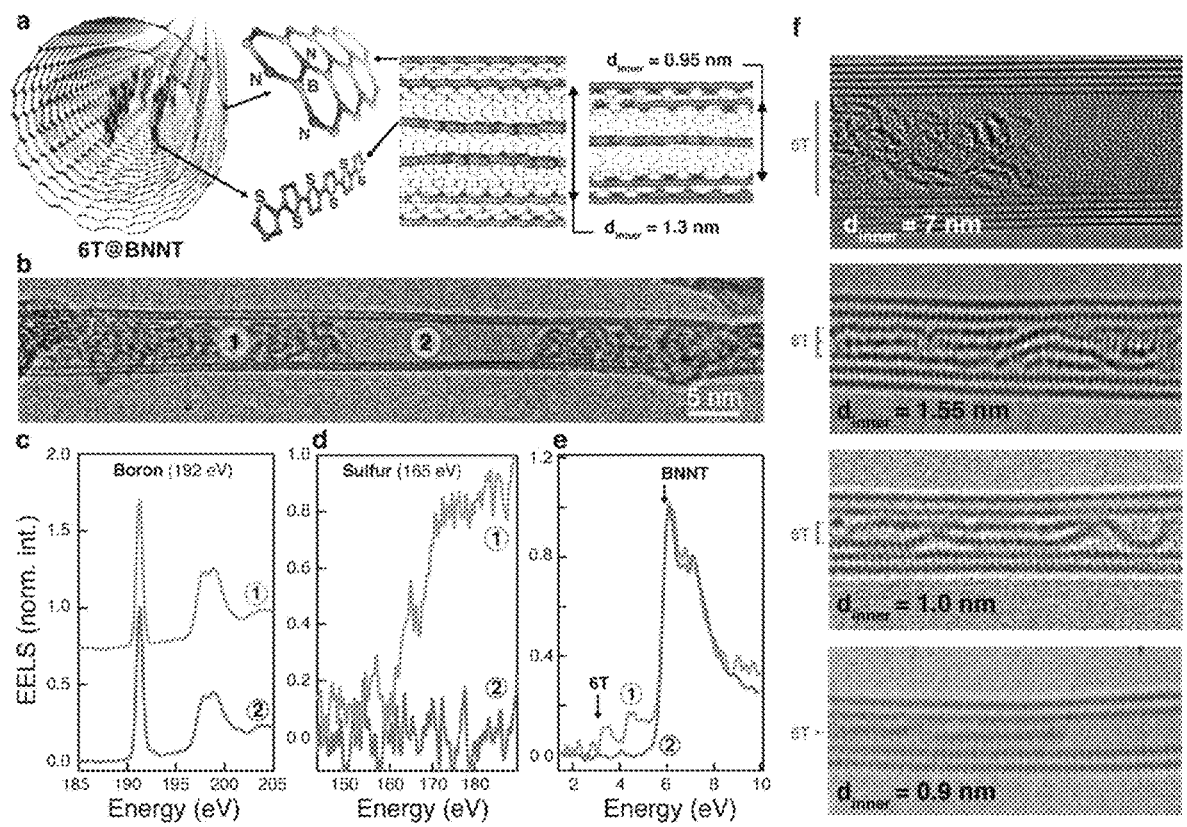
FIG. 2: Structural properties of α-sexithiophene (6T) encapsulated inside a double-walled boron nitride nanotubes (6T@BNNTs). a, Schematic view of the structure of 6T molecules encapsulated in double-wall BNNTs. b, HRTEM image of a partially filled 6T@BNNT suspended on a Molybdenum-SiO2 TEM grid. c and d, Chemical analysis of selected areas (1) and (2) in (b) using core-loss STEM-EELS at the boron K-edge (192 eV) and sulfur L2,3-edge (165 eV). e, Measurements of the energy levels in the same two areas by STEM-EELS in the 1-10 eV energy range. f, HRTEM images of 6T molecules inside BNNTs of different diameters. The HRTEM and STEM-EELS data are recorded at 80 kV.
Figure 13:
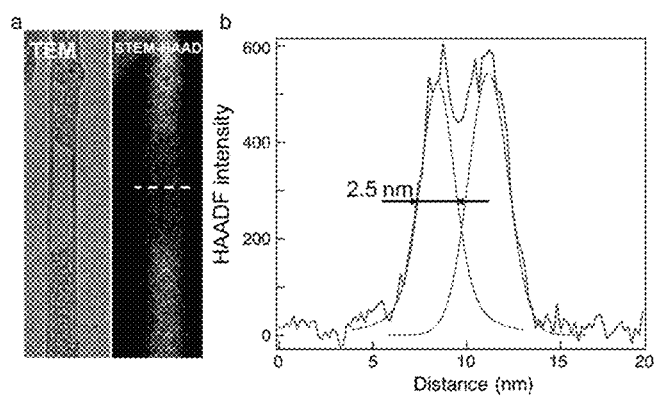
FIG. 13: a TEM and STEM-HAADF (left and right respectively) images at 80 kV of a double walled boron nitride partially filled with 6T molecules. b HAADF profile of the empty part of the BNNT along the cross section dashed line indicated in (a). The deconvolution of the wall gives a special resolution of about 2.5 nm of the STEM probe at 80 kV
Figure 14:
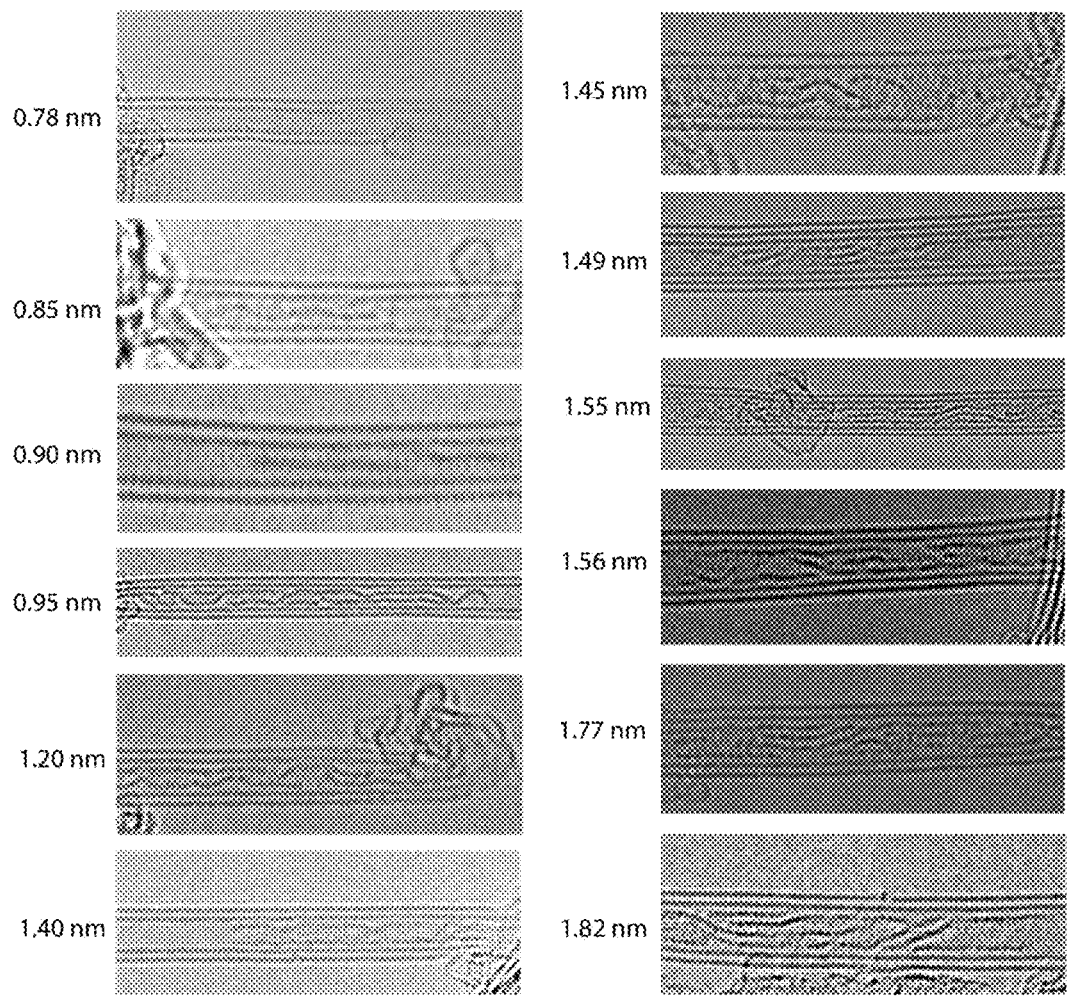
FIG. 14: High Resolution image recorded at 80 kV of 6T@BNNT for various inner diameters, highlighting the progressive ordering of the molecules as a function of the 1D confinement. Most of the BNNT observed are filled or partially filled with molecules. Only the observed BNNT having an inner diameter bellow 0.8 nm are non-encapsulated, that represent probably the diameter limit for encapsulating 6T molecules in BNNT.

Such drastic changes in optical properties strongly suggest that the inner space of the BNNT has templated an ordering of the encapsulated dyes into well-defined aggregates. To test this hypothesis, we examine the morphological arrangements of the dyes using High Resolution Transmission Electron Microscopy (HRTEM). FIG. 2 shows images of double- and multi-walled BNNTs deposited onto a Molybdenum-$SiO_2$ (Mo/$SiO_2$) TEM grid after applying a filling process in solution with 6T molecules. More examples of HRTEM are also shown in the Supplementary, FIG. 14. To determine that the filling material is composed of 6T molecules, preliminary experiments were performed using Scanning Transmission Electron Microscopy and Energy Electron Loss Spectroscopy (STEM-EELS) recorded at 80 kV to gain information on the chemical composition (core-loss) and the near-band edge response (low-loss) of the filling materials with a spatial resolution of around 2.5 nm (Supplementary FIG. 13). The HRTEM image in FIG. 2b provides distinct responses in the empty and filled regions (open circles 1 and 2, respectively), which are presented in FIGS. 2c-e. The boron K-edge from the shell structure of the BNNT at 192 eV is measured, as expected, in both regions 1 and 2, but a new contribution is detected only in region 1 at the energy corresponding to the L2,3-edge of the sulfur atoms in a 6T molecule. Local energy loss measurements in regions 1 and 2 (FIG. 2e) show the expected transitions at around 3 eV (region 1) for the HOMO-LUMO gap of 6T molecules and at 5.5 eV (region 2) for the BNNT band gap. Consistent to other HRTEM studies on similar oligothiophenes encapsulation inside SWCNTs, the EELS presented here confirm that the 6 Ts are encapsulated inside BNNTs.

The HRTEM images presented in FIG. 2f show a progressive ordering of the 6T dyes, from disordered assemblies to well-aligned individual molecules, for inner diameters ($d_{inner}$) going from 7 nm down to 0.9 nm, respectively. A key result for this study is the presence of single and double aggregates of 6T molecules inside BNNTs having the smallest $d_{inner}$. These aggregates are nicely resolved in FIG. 2f as short sticks (pointing orange arrows) located inside BNNTs of $d_{inner}$=0.9, 1.0 and 1.55 nm for single, double and triple aggregates, respectively. Note that the double aggregate is schematically shown in FIG. 2a. It is clear from the TEM experiments that high confinement (i.e. low $d_{inner}$) induces molecular ordering and alignment along the nanotube axis. A cavity of $d_{inner}$=4 nm is, for instance, much larger (about twice) than the length of the molecule and provides higher degrees of freedom to accommodate various assemblies, whereas $d_{inner}$=0.9 nm (the smallest diameter observed in our samples) provides just enough space to fit one molecule in a head-to-tail type of stacking.

The assembly of elongated dyes inside BNNTs into aligned and structured aggregates is consistent with what was observed previously with SWCNTs. However, the distribution of the inner dimeters in our BNNT samples is much wider than SWCNTs, which brings more complexity to the population distribution of aggregates in BNNTs. Depending on the diameter, both complex or simple alignments between adjacent molecular transition dipole moments can be formed, which lead de facto to a mixture of aggregation states in our samples. As seen in the HRTEM images (FIG. 2f), the head-to-tail stacking of the encapsulated dyes in small diameter BNNTs would coexist in solution with the face-to-face arrangements in larger diameter BNNTs, giving in some cases double and triple rows of molecules. The former morphology corresponds to the emblematic J-aggregation state, while the latter is consistent with a H-aggregate, each promoting specific intermolecular interactions. Considering the diversity of morphologies in our samples, one should therefore expect specific optical signatures associated to possible H-like, J-like and HJ-states, as well as other photo-physical phenomena such as Davidov splitting, excimers and energy transfers. By shifting the excitation wavelengths well below the gap of free dyes (arrows, FIG. 1), we clearly see for instance new vibronic bands that are strongly shifted towards the NIR. This reflects sub-populations of aggregation states that are consistent with J- or HJ-like bright emitters in small diameters BNNTs. The case of P7 is particularly interesting because the emission is red-shifted by more than 600 nm, which is surprising for a dye that usually fluoresces in the visible. Understanding the bands and vibronic structures in such a complex mixture of aggregates is obviously not straight forwards and clearly outside the scope of this work. It would require a powerful approach to disentangle each population of aggregates using for instance sorted BNNTs by inner diameters.

Figure 3:
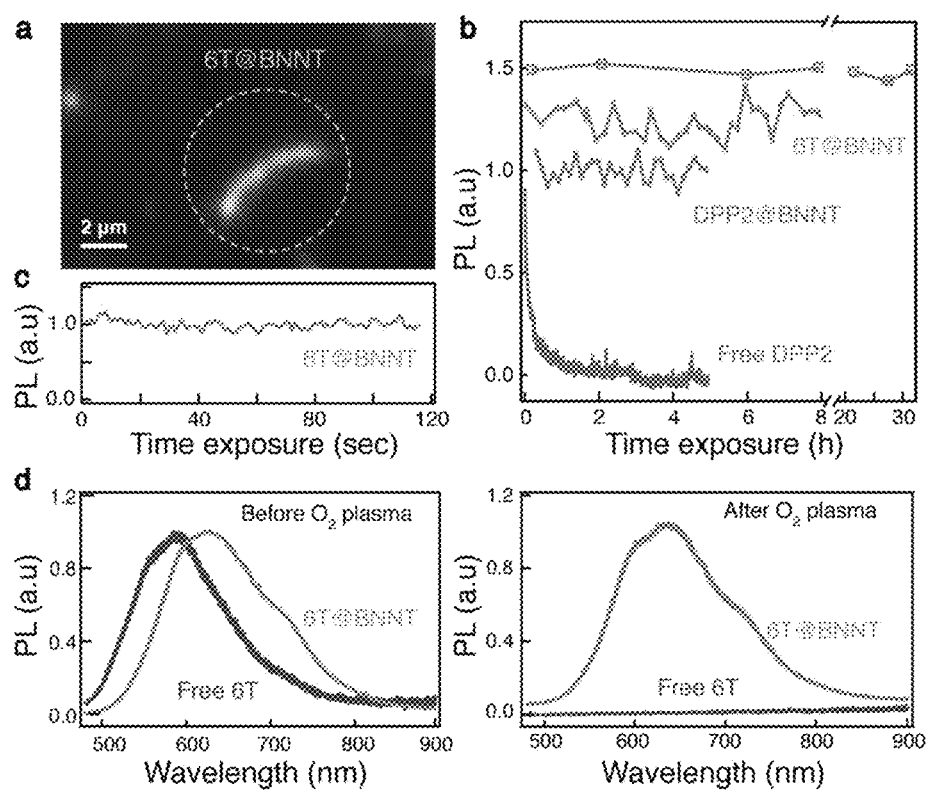
FIG. 3: Photostability and chemical resistance of 6T@BNNTs. a, Integrated luminescence imaging of a typical microbundle of a 6T@BNNT deposited on a Si/SiO$_2$ substrate ($\lambda_{ex}$=532 nm). The time acquisition is 0.2 sec and the laser fluence is 1.2 µW·µm$^{-2}$. b, Time evolution of the integrated PL of isolated bundles of 6T@BNNTs and DPP2@BNNTs on a Si/SiO$_2$ surface, compared to free DPP2 photoexcited under a fluence of 1.2 µW·µm$^{-2}$ at $\lambda_{ex}$=532 nm (long pass filter at 533 nm). c, PL intensity recorded at time intervals of 0.5 sec. d, PL spectra ($\lambda_{ex}$=473 nm) of free 6T and 6T@BNNT deposited on a substrate recorded before (left) and after (right) a 100 W treatment to oxygen plasma for 10 minutes.
Figure 7:
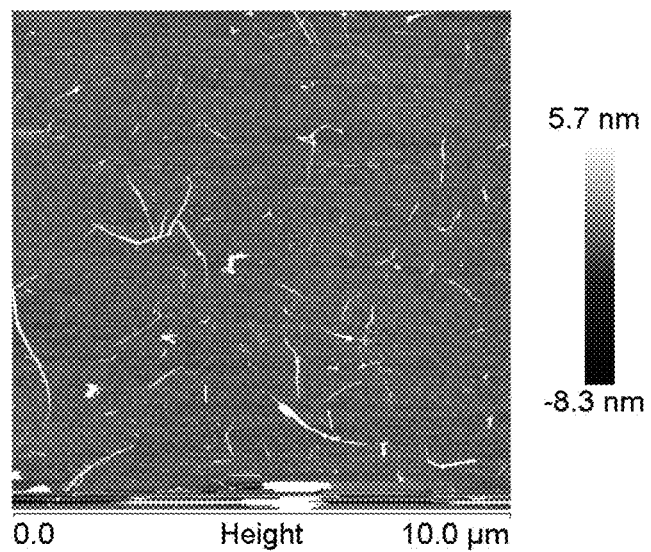
FIG. 7: 10×10 µm AFM image of BNNTs deposited on a Si/SiO2 substrate after purification.

The passivation of the dyes with the crystalline dielectric sheath of the BNNT walls is tested next using stability measurements against photo-bleaching and chemical reactions. To do so, we compared in FIG. 3 the PL properties of free dyes with that of individual or small bundles of 6T@BNNTs deposited on an inert Si/SiO$_2$ substrate in ambient conditions. A typical AFM image is shown in FIG. 7. Note that an oxide thickness of ~300 nm was chosen to avoid destructive optical interference with the substrate. To gain statistics, a global hyperspectral imager (RIMA™, Photon etc.) was used to photo-excite uniformly a large area of the sample (200×200 µm$^2$) with continuous laser light at $\lambda_{ex}$=532 nm. This configuration has given us a large statistical ensemble of measurements on individualized bundles of 6T@BNNT as a function of exposure time and fluence conditions. As an example, FIG. 2a shows a zoomed view of the PL image of a 5 µm long bundle at a laser fluence typical for bio-imaging (1.2 µW·µm$^{-2}$). In FIG. 3b, the PL signal of the bundle shows no noticeable intensity loss with exposure time, even after exposure for more than 8 hours in air. This interesting result indicates a clear resistance against photo-bleaching, which is also demonstrated with the DPP nanohybrids in FIG. 3b. The result contrasts with the fast fading PL signal (in red) of free dyes (not encapsulated) dispersed on the substrate. As expected, the half lifetime of the integrated emission ($\tau_{1/2}$) of free dyes is only few minutes, which is typical for an organic dye, whereas individual dyes@BNNT bundles produce unaltered PL after more than 30 hours. The measurement is only limited here by our setup to a factor of 1×10$^4$. Furthermore, PL images taken at the level of a single dye nanohybrid with a frame rate of 0.5 sec indicate no blinking under a fluence of 1.2 µW·µm$^{-2}$ at $\lambda_{ex}$=532 nm (FIG. 2c). These photostability results are impressive considering that this is a lower bound estimate.

The chemical stability of the nanohybrids is tested using individualized 6T@BNNT bundles on Si/SiO$_2$ exposed to an oxygen plasma of 100 W for 10 minutes. No significant change in the PL spectral shape and intensity is detected after this treatment, whereas free 6T molecules on Si/SiO$_2$ have completely vanished (FIG. 3d). The enhanced stability of the encapsulated dyes has also been observed upon thermal annealing up to 350° C. in air and using piranha solutions (not shown). These results demonstrate that the 6T@BNNT is far more stable than free 6T dyes. The chemical and physical stability experiments have been repeated on a number of Dyes@BNNT nanohybrids of different lengths deposited on substrates or dispersed in a solution (See e.g. Supplementary Figs. 10 and 11). All of the results lead us to the same conclusion, which underlines the tremendous gain in stability inferred by the confinement of the 1D cavity of BNNTs.

Figure 4:
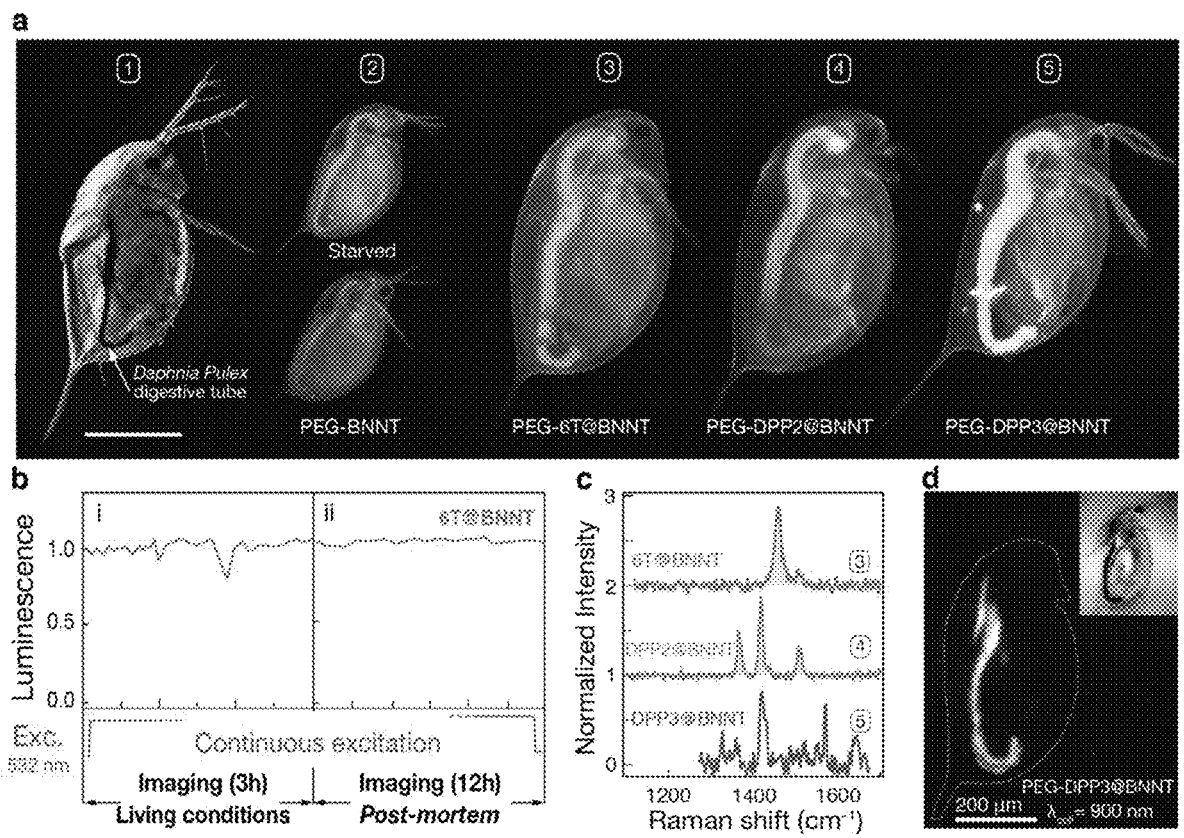
FIG. 4: Dyes@BNNTs as hypermodal nanoprobes illustrated for Vis-NIR bio-imaging of *Daphnia pulex*. a, Z-reconstructed confocal optical image of a *Daphnia* immobilized in Leica medium (#1). PL images recorded through a fluorescence microscope mounted with a UBG filter and 10× objective lens of living starved *Daphnia* (top #2) and after incubation in a solution of unfilled BNNTs (bottom #2), 6T@BNNTs (#3), DPP2@BNNTs (#4) and DPP3@BNNTs (#5). b, Luminescence intensity time-lapses of dyes@BNNTs, (i) in living conditions, (ii) in post-mortem conditions. c, Raman spectra at $\lambda_{ex}$=532 nm taken in the region of the digestive tube of *Daphnia* for #3 and at $\lambda_{ex}$=633 nm for #4 and #5. d, PL image of a living *Daphnia* collected at a wavelength of 900 nm using an excitation at $\lambda_{ex}$=532 nm. Inset: Optical image of the *Daphnia*. The scale bar is 200 µm for images #1, #3-#5 and 400 µm for #2.
Figure 8:
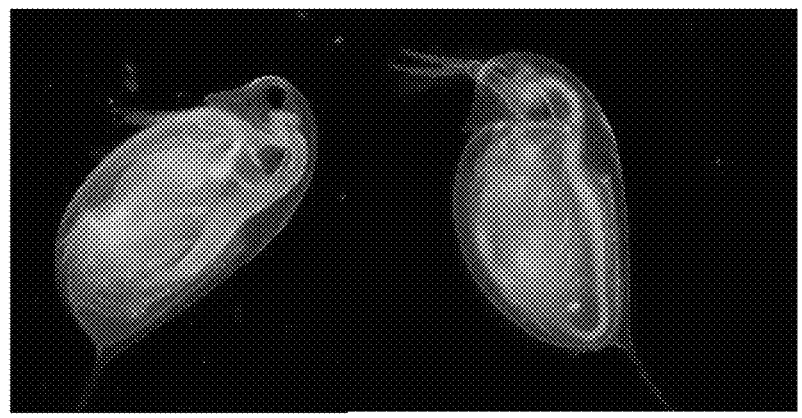
FIG. 8. Luminescence image using UBG filter of *Daphnia* before (left) and after (right) cleaning of digestive tube (starved).
Figure 9:
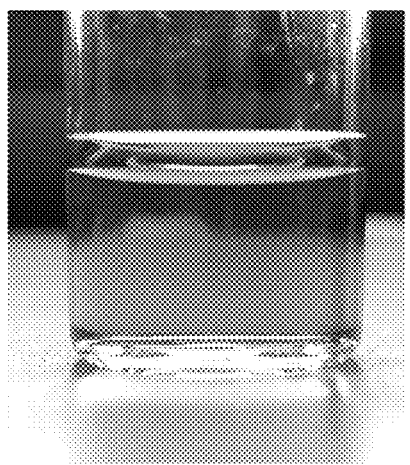
FIG. 9. living *Daphnia* after an incubation of 12 h in a solution of DPP2@BNNT.

The impressive robustness and fading-free properties of the Dyes@BNNT are appealing for bio-imaging applications. FIG. 4 presents an example of the use of nanohybrids to make optical nanoprobes for imaging living *Daphnia pulex* microorganisms in water—see bright-field image in FIG. 4a #1. *Daphnia* (also called water fleas) are common planktonic crustaceans, which find use as chemical sensors in ecotoxicology studies, thanks to their high sensitivity to water quality. To acquire the bio-images (FIG. 4a #2-5), we first solubilized the Dyes@BNNTs in a water-based living medium called FLAMES, using a poly (ethylene) glycol derivative (mPEG-DSPE) (Supplementary Section 2.9). We then performed a first incubation test by placing a *Daphnia* in different FLAMES containing either free 6T, only PEG-BNNTs, or PEG-dyes@BNNTs (see Supplementary Table S1 and FIG. 8). After an incubation time of only few minutes, all daphniids exposed to free 6T were found dead. This is consistent with the known toxicity of the dyes to living organisms, as evidenced since the early 20$^{th}$ century by many studies. On the contrary, all of the *Daphnia* assays incubated with both PEG-BNNT and PEG-dyes@BNNT remain alive and active after incubation times ranging from a few minutes to 36 hours at concentrations between 10 and 50 µg·ml$^{-1}$ (Supplementary FIG. 9). This underlines the multiple roles of the BNNT host: i) Stabilizing the PL signal from the nanoprobe, ii) acting as a protective barrier against ROS, and iii) reducing dye toxicity to the living organisms. Living daphniids were imaged under a fluorescence microscope equipped with UBG filter and a 10× objective. *Daphnia pulex* incubated with PEG-BNNTs (i.e. no dye, FIG. 4a #2 down) presents similar signal than that observed from non-incubated *Daphnia* (FIG. 4a #2 top). This natural blue-green signal originates from the auto-fluorescence of the tissues in FLAMES through the UBG filter, which disappears after death or after few minutes only of photo-bleaching. In contrast, Daphniids incubated with PEG-Dyes@BNNTs (FIGS. 4a #3-5) exhibit a distinct digestive tube emitting bright signals assigned to the spectral line-shape of each PEG-Dyes@BNNTs nanohybrids.

In a second set of experiments, we investigated the photo-stability of the nanoprobes during in-vivo PL imaging of *Daphnia pulex* under continuous light excitation. Daphniids were maintained alive during the first 3 hours of the time-lapse by adding more FLAMES to maintain temperature and compensate water evaporation under the microscope. The PL intensity, recorded every 3 minutes at 6 different points of the digestive tube (FIG. 4a), remains flat with time, which indicates that bleaching is suppressed in such continuous photoexcitation despite the fact that the nanoprobes are in close contact with the ROS present in the water-based medium of the digestive tube of Daphniids. The brief and temporary drops of signal at 1 h and 3 h are attributed to sudden movements of the *Daphnia* in the exiguous swimming pool under the microscope objective (FIG. 4b). Even after death, which is typically caused by a drying of the FLAMES medium, the signal of the nanoprobes remain stable for an additional 12 hours of continuous excitation/imaging without any noticeable loss of signal (FIG. 4b). Interestingly, the Raman spectra in FIG. 4c, recorded at the level of the digestive tube of *Daphnia* #4 and #5, show that the specific vibrational fingerprint of the encapsulated 6T (or DPP) in BNNTs remain intact. This signal can be readily extracted and identified from the luminescence signal, thanks to the resonance enhancement of the dyes at $\lambda_{ex}$=532 nm. This experiment demonstrates that the encapsulated dyes are not altered in the digestive tube of the living *Daphnia* and that they are highly photostable, giving further statistics of the effective passivation by the BNNT hosts.

The capability to probe both the fluorescence and Raman scattering of different nanoprobes in-situ over a timescale of many hours is interesting for bio-imaging using multimodal probes. Similar to the work on carbon nanotubes based NIR nanoprobes [Welsher, K. et al. A route to brightly fluorescent carbon nanotubes for near-infrared imaging in mice. *Nature Nanotech.* 4, 11, 773-780 (2009)], which emit at wavelengths beyond 900 nm, we performed experiments using a DPP3@BNNT incubated in *Daphnia*. By changing the dyes, we were able to easily extend the PL emission of the nanoprobes (FIG. 4d) to the NIR I optical bio-window [Hong, G., Antaris, A. L., and Dai, H. (2017). Near-infrared fluorophores for biomedical imaging. Nature Biomedical Engineering, 2017, 1(1), 1-22]. From this and the results in FIG. 1, it is clear that the emission properties of DPP2@BNNT would allow excitation in the NIR I and detection in the NIR II, which is of interest for deep imaging studies on animals such as mice.

Figure 5:
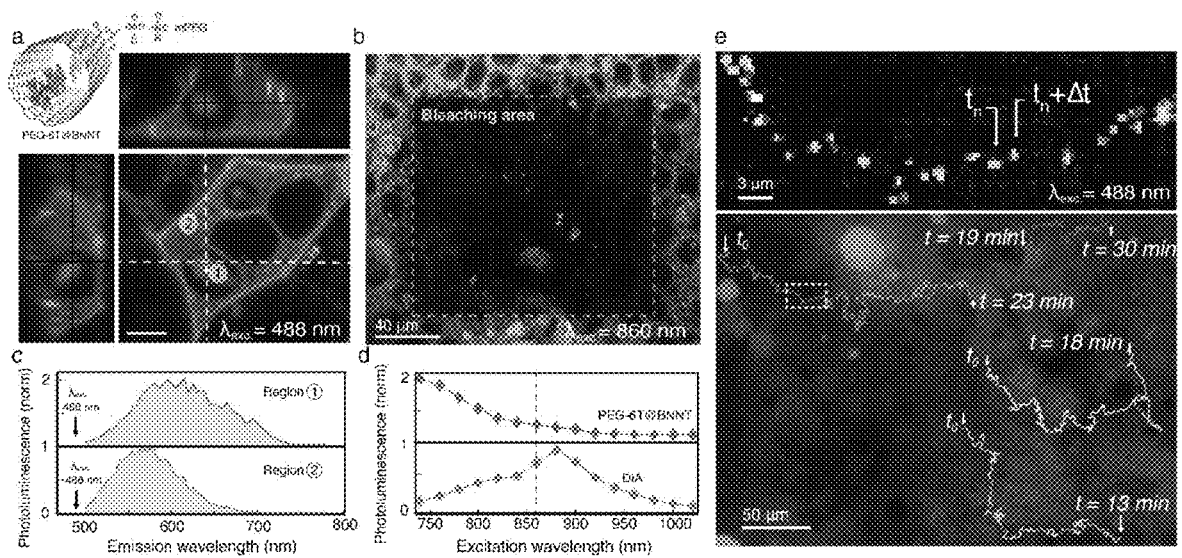
FIG. 5: Imaging of Dyes@BNNTs in a HuH6 cells mat. a Hyperspectral and confocal fluorescence imaging of liver cells incubated with PEG-6T@BNNT for 24 hours and with DiA for 10 mins before imaging. The red and green channels correspond to the integrated intensity from 600 nm to 780 nm and 490 nm to 520 nm, respectively. b Hyperspectral two-photon fluorescence image of fixed hepatoblastoma cells previously incubated for 24 hours with PEG-6T@BNNTs. The dashed line highlights a bleaching test area where the DiA and the PEG-6T@BNNTs were illuminated in two-photon imaging conditions at $\lambda_{ex}$=860 nm for 30 mins. The red and green channels correspond to the integrated intensity from 645 nm to 715 nm and from 500 nm to 530 nm, respectively. c Fluorescence spectra extracted from the hyperspectral datacube of regions 1 and 2 in (a). d Two-photon fluorescence excitation profiles of the DiA and PEG-6T@BNNT extracted from an hyperspectral fluorescence image datacube. e Top: Tracking of a single PEG-6T@BNNT nanoprobe in confluent HuH6 cells using a superposition of luminescence images extracted every 30 sec from a time-lapse datacube (Δt=650 msec, $\lambda_{ex}$=488 nm). Bottom: Full trajectory reconstruction using a tracking algorithm (see Supplementary) of the four PEG-6T@BNNTs detected within the field of view.

To further assess a possible toxicity of the Dyes@BNNT, we performed an additional set of experiments at the scale of a cell. We incubated 10 μg·mL$^{-1}$ of a PEG-6T@BNNT solution for 24 hours with human hepatoblastoma HuH6 cells, which is one of the model cell lines used for toxicology studies. After removal of the media containing Dyes@BNNTs, the cells membranes was revealed using 5 μL·mL$^{-1}$ of DiA fluorophore for 10 mins (see Supplementary). FIGS. 5a and 5c show fluorescence spectra consistent with DiA (green) and PEG-6T@BNNT (red) separated in the regions 2 and 1, respectively. In these conditions, we observe that the DiA are fixed, as expected in the cell membranes, while the nanoprobes are internalized by the cells and accumulated in endocytoplasmic compartments. In addition, a positive green Calcein staining assay shows no lethality of the cells in this time scale (see FIG. 12). In FIG. 5b, we investigated the imaging capability and photostability of the PEG-6T@BNNT using two-photon imaging techniques on HuH6 cells fixed after an incubation of nanoprobes followed by DiA at a concentration of 10 μg·mL$^{-1}$ and 5 μL·mL$^{-1}$, respectively (see Supplementary). The fluorescence of both the DiA and PEG-6T@BNNT, as a function of the excitation wavelength between 740 nm and 1020 nm, is shown in FIG. 5d. The resonance maximum of DiA is measured at 880 nm, which is distinct from the resonance of the PEG-6T@BNNT located at ~740 nm, a position similar to that of functionalized polythiophene. A wavelength centred at 860 nm was used to expose simultaneously DiA and PEG-6T@BNNT in the bleaching test area highlighted in FIG. 5a (dashed line) with two-photon imaging conditions during 30 mins (400 Hz, laser output power of 2.55 W). To directly compare exposed and non-exposed cells, FIG. 5b presents a two-photon hyperspectral fluorescence image taken in a field of view slightly larger than the photobleaching test area. The exposed DiA have been significantly photo-bleached while the PEG-6T@BNNTs are still strongly fluorescent without loss of signal. This result highlights the photostable response of the Dyes@BNNT against the stringent two-photon illumination conditions. This result demonstrates long term (day-scale) monitoring without the need of periodic injection of contrast agents.

Finally, the last experiment tracks individual Dyes@BNNT in cellular environment. Because of their 1D architectures, these nanoprobes should have similar diffusion properties than individual SWCNTs, which are advantageous for studies in biological media. Another solution of PEG-6T@BNNT with an excess of PEG to lower the interaction with the cell membrane (0.5 μg·ml$^{-1}$ in DMEM), we incubated the nanoprobes for 24 hours followed by rinsing to remove none interacting nanoprobes with the confluent cell mat (see Supplementary). Time-lapse luminescence during 30 mins with a time interval Δt of 650 msec between two images is shown in FIG. 5e. The superposition of few sequential fluorescence images of a single 6T@BNNT nanoprobe, extracted for clarity from the datacube every ~10 sec, is displayed in the top panel of FIG. 5e. By using a single object tracking algorithm, we reconstructed the trajectory of four individual nanoprobes in the FIG. 5e (bottom panel). As expected, the nanoprobes are clearly photostable and the diffusion length is larger than the size of the cells. We don't observe internalisation of the nanoprobes in this case, which is probably due to the high coverage of PEGs promoting higher furtivity of the nanoprobes.

Previous works on the functionalization of multi-walled BNNTs have shown that BNNTs are appropriate templates to develop biocompatible nanostructures for drug delivery [J. Niskanen, I. Zhang, Y. Xue, D. Golberg, D. Maysinger, F. M. Winnik, *Nanomedicine* 2016, 11, 447; G. Ciofani, G. G. Genchi, I. Liakos, A. Athanassiou, D. Dinucci, F. Chiellini, V. Mattoli, *Journal of Colloid and Interface Science* 2012, 374, 308]. Here, we have highlighted the potential use of dyes@BNNT as a fluorescence nanoprobe giving high brightness, low toxicity and exceptional stability. Because the preparation of dyes@BNNT is simple and general, we trust that the approach can be further expanded to include other dyes so as to produce a library of nanoprobes with tuneable colours from the visible to the NIR I and II for deeper imaging into living organisms. Building on a constantly evolving knowledge on BNNT materials, it is expected that further control on the confinement of the dyes inside dye@BNNT will be possible, which is key to control aggregation states giving more advanced fluorescence properties, such as coherence effects or single photon emission.

Methods

The boron nitride nanotubes (BNNT) used in this work are provided by BNNT™. See Supplementary Section 2.1 and 2.2 for details on cleaning and encapsulation of BNNTs. Briefly, the BNNT powder was sonicated in dimethylformamide (DMF) until complete dispersion, and filtrated on a PTFE filter (0.2 μm pore size). The obtained film was annealed at 800° C. for 2h under atmospheric conditions. About 5 mg of dyes and 20 mg of purified BNNTs were dispersed sequentially in 20 mL or 300 mL of toluene, depending on the dye used, by sonication. The solution was then refluxed at 80° C. or 115° C., again depending of the dyes used, to activate the encapsulation. The solution was finally washed in toluene and DMF at least 10 times to remove the free dyes molecules, until the filtrate became colorless. The Absorption spectra presented in FIG. 1 were acquired using a Bruker vertex v80 spectrometer with CaF2 beamsplitter and Si and GaP detector. The fluorescence spectra presented in FIG. 1 were recorded using a spectro-fluometer from Horiba JY equipped with PMT and InGaAs detectors.

For experiments on individualized Dyes@BNNTs on surface, the Dyes@BNNTs were suspended in N,N-dimethylformamide (DMF) and diluted as needed, typically at a concentration of ~0.1 mg/mL. This solution was spin-coated at 3000 rpm on a cleaned Si/SiO$_2$ substrate with aminopropyltriethoxysilane (APTES) functionalization.

For experiment with *Daphnia*, an incubation solution was prepared by dispersing Dyes@BNNT in FLAMES culture medium at a concentration ranging from 5 to 100 μg/ml. Adult individuals of *Daphnia pulex* (clones DISP 1312) were kept at 22° C. in FLAMES with algae for 4 days before the experiment, allowing for a new reproducing cycle. Then, the specimens were transferred to a FLAMES medium algae-free and remained there for 1 day at minimum to clean the digestive system and limit any PL from algae during the images/time lapse acquisition. Daphniids are then placed in the incubation solution for the required time. More details on the experiments with *Daphnia* and characterizations of the samples are provided in Supplementary Section 2.9 and 3.

The AFM images were produced using a Dimension 3100 microscope. The Raman/PL measurements were taken from different set-ups depending on the experiments and these instruments and conditions are summarized in Table S2. In summary, luminescence images and photobleaching experiments were performed at $\lambda_{ex}$=532 nm using the Raman/PL mapping system RIMA™ (Photon Etc) using a 100× objective and a laser power ranging from 0.5 μW·μm$^{-2}$ to 80 μW·μm$^{-2}$. The fluorescence images on *Daphnia* were acquired with an Olympus confocal microscope equipped with a U-RFL-T mercury light source, a BX-UCB controller and a DP71 digital camera. The images were acquired with a 10× objective and UBG, TRITC and TXRED filters. The acquiring conditions were: Exposure time: 1/20 sec and ISO 200 sensitivity. Z-stack of 20 images to probe the volume of the *Daphnia* was acquired by confocal imaging and stacked using the Auto-blend function in Phostoshop. The hyperspectral and confocal fluorescence images on confluent HuH6 hepatoblastoma cells, previously incubated for 24 hours with PEG-6T-BNNT at a concentration ranging from 0.5 to 10 μg·mL$^{-1}$, were recorded on two different setup: a Leica microscope SP8 WLL2 using a HCX Plan Apo CS2 63× oil NA 1.40 objective or a HC PL FLUOTAR 10×/0.30 DRY objective and a Leica TCS SP5, using either Argon laser or Mai Tai HP laser (SpectraPhysics, Irvine, USA) and a HC PL APO CS2 40.0×1.30 OIL objective.

Annex A

Supplemental Information

1) Materials
  1.1 Dyes@BNNT synthesis
  1.2 Experiments with *Daphniids*
  1.3 Experiments with human hepatoblastoma cells
2) Methods 2.1 Cleaning and opening of the BNNT
  2.2 Encapsulation in BNNT powder of sexithiophene (6T) and DPP molecules
  2.3 Solubilisation of Dyes@BNNT in aqueous solutions
  2.4 Aminopropyltriethoxysilane substrate (APTES) on Si/SiO$_2$
  2.5 Deposition of BNNT on substrates with APTES
  2.6 Encapsulation of 6T and DPPx into BNNT deposited on Si/SiO$_2$ substrates
  2.7 Encapsulation of 6T into BNNT on TEM grid (Mo/SiO$_2$)
  2.8 Photobleaching experiments of 6T@BNNT and DPP2@BNNT
  2.9 Incubation of 6T@BNNT and DPP3@BNNT in *Daphnia*
  2.10 Photobleaching experiments on Dye@BNNT assemblies
  2.11 Preparation of hepatoblastoma HuH6 cells
  2.12 6T@BNNT experiments with human hepatoblastoma HuH6 cells
3) Characterization
  3.1 Characterization by AFM
  3.2 Characterization by Raman and Photoluminescence.
  3.3 Characterization by HR-TEM and TEM-EELS
  1) Materials
  1.1 Dyes@BNNT synthesis. The boron nitride nanotubes (BNNT) were provided by BNNT™ and Sigma-Aldrich. Only reagent grade solvents were used. 3-aminopropyltriethoxysilane (APTES) (99%) and α-sexithiophene (6T) were purchased from Sigma-Aldrich and used as received. Oligothiophene derivatives, such as 3,6-Bis-[2,2]bithiophenyl-5-yl-2,5-di-n-oc-tylpyrrolo[3,4-c]pyrrole-1,4-dione (DPPX), were synthesized according to the procedure in Reference [A. B. Tamayo, M. Tantiwiwat, B. Walker, T.-Q. Nguyen, *J. Phys. Chem. C*, 112, 15543 (2008)].

1.2 Experiments with Daphniids. Culture medium—FLAMES—5 L, mix of algae dispersed into FLAMES. DSPE-m PEG, (methoxy-poly(ethylene glycol)-1,2-distearoyl-sn-glycero-3-phosphoethanolamine-N conjugates), mw 5000, from Sigma. The *Daphnia pulex*—DISP1312—clone #1312 from Disputed Pond in Ontario (coordinates: 42.17N, 83.03 W). Adhesive glass slides model APEX Superior and pre-cleaned white glass micro slides (25.5 mm×75.5 mm×1 mm) were purchased from Surgipath Leica biosystems. Reference number: 3800080 white—LOT 4900034605.

1.3 Experiments with human hepatoblastoma cells. HuH6 human hepatoblastoma cells from Culture media—DMEM low glucose (PanBiotech, P04-01550) were used as is. Fast DiA fluorophore (ThermoFischer Scientific D7758), paraformaldehyde PFA (Alfa Aesar, 43368.9M) (16% diluted to 4% in culture medium), Calcein-AM (ThermoFisher, C3100MP), glass-bottom 24-well plates (Greiner Bio One, 738-0031) were used for these experiments.

Figure 6:
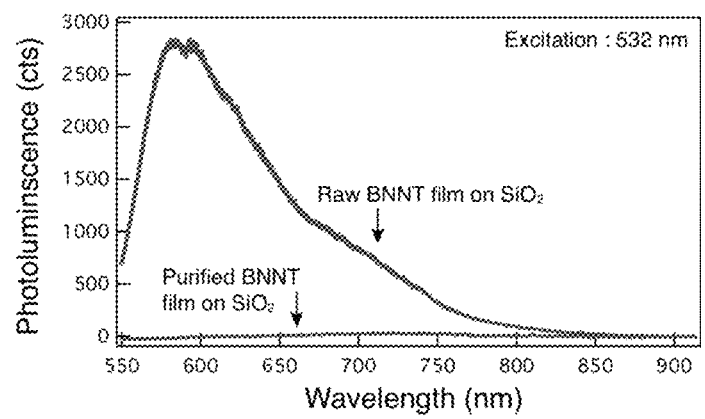
FIG. 6: Photoluminescence spectra of BNNT deposited on Si/SiO2 before and after purification. Each spectrum corresponds to the average contribution from 5 areas on each sample. The excitation is at a wavelength of 532 nm.

2) Methods
  2.1 Cleaning and Opening of the BNNT.
BNNT powder. The BNNT powder was sonicated in N,N-dimethylformamide (DMF) until a complete dispersion was obtained. The solution was then filtrated on a PTFE filter (0.2 μm pore size) and the film of the residue was annealed at 800° C. for 2h under atmospheric conditions. After this cleaning procedure, we measured a negligeable parasite luminescence signal from BN impurities, $B_2O_3$, and defects (see FIG. 6).

2.2 Encapsulation in BNNT (Powder) of Sexithiophene (6T) and DPP Molecules.

6T@BNNT: In a typical experiment, 5 mg of 6T was added to 300 mL of toluene and dispersed by sonication during 2h. 20 mg of purified BNNT powder was added to the encapsulation solution and refluxed at 115° C. (6T) for 24 h. The solution was then washed in toluene and DMF at least 10 times to remove free (not encapsulated) 6T, until the filtrate became colorless.

Finally, the sample was dispersed in DMF at the appropriate concentration for subsequent characterisation.

DPPx@BNNT: 5 mg of DPPx (DPP2 or DPP3) was solubilized in 20 mL of toluene and 5 mg of purified BNNTs were added to the encapsulation solution. The solution was sonicated for 30 minutes and refluxed at 80° C. overnight. The washing and dispersion steps are as described above.

2.3 Solubilisation of Dyes@BNNT in aqueous solutions. For interaction with the *Daphnia*, BNNTs were filtrated and rinsed in spring water at least 3 times. They were subsequently dispersed in a solution of mPEG-DSPE in spring water, adapted from a previous report, at an appropriate concentration [V. H. Lee, D. Zhang, Y. K. Yap, Functionalization, dispersion and cutting of boron nitride in water, *J. Phys. Chem. C*, 116, 1798-1804 (2012)].

2.4 Aminopropyltriethoxysilane substrates (APTES) on Si/SiO$_2$. The Si/SiO$_2$ substrates were cleaned by successive sonication of 10 minutes each in acetone and isopropanol (IPA). The substrates were then immersed in piranha solution for 20 min, rinsed in water, and dried in a flow of N$_2$. Finally, the substrates were placed on glass slides suspended above a crystallization dish containing 1 mL of APTES. The desiccator was vacuum pumped for one minute and the chamber was sealed for an additional thirty seconds. The APTES layer was annealed in air for 45 minutes at about 100° C. in a conventional oven.

2.5 Deposition of BNNT on Substrates with APTES

Raw BNNTs were suspended in DMF and diluted as needed, typically at a concentration of ~0.1 mg/mL. This solution was spin-coated at 3000 rpm on a substrate covered with APTES. Atomic Force Microscopy was used to control the quality of the BNNT deposition (FIG. 7).

2.6 Encapsulation of 6T and DPPx into BNNTs deposited on Si/SiO$_2$ substrates. The sample was treated with concentrated nitric acid for 5 min and then baked at 800° C. under vacuum to remove water. The sample was then immediately used for encapsulation. The substrates covered with BNNTs was gently placed into a flask equipped with a condenser and the (e.g. DPPx) solution was refluxed overnight at 115° C. (6T) or 80° C. Following the encapsulation step, the sample was rinsed in fresh toluene, then IPA, and finally dried in N$_2$.

2.7 Encapsulation of 6T in BNNT for TEM grid (Mo/SiO$_2$). 5 mg of raw powder of BNNTs was first mechanically grinded then dispersed into 15 ml of DMF using an ultrasonic bath for one hour. About 20 uL of this solution was drop-casted on a Molybdenum grid with SiO$_2$ membrane decorated with holes. The deposited BNNTs were then annealed at 350° C. under atmospheric conditions, followed by another anneal under vacuum at 800° C. for two hours. The grid was inserted in the 6T encapsulation solution at 115° C. for 6 hours. Following the encapsulation, the grid was rinsed for a few seconds in DMF, cleaned using an oxygen plasma (100 W, 10 minutes) and a piranha treatment (2 minutes) to completely remove the excess of non-encapsulated dyes.

2.8 Photobleaching experiments of 6T@BNNT and DPP2@BNNT. BNNTs were first deposited on Si/SiO$_2$ substrates then encapsulated with 6T or DPP2 molecules using the protocol described in section 2.6. The integrated intensity of tracked isolated Dyes@BNNT was then recorded using the hyperspectral Raman/luminescence imager RIMA™ (Photon etc.) at an excitation wavelength of 532 nm. The time acquisition is 0.2 sec and the laser fluence is 1.2 µW·µm$^{-2}$.

2.9 Incubation of *Daphnia pulex* with 6T@BNNT and DPP3@BNNT. *Daphnia* is a freshwater crustacean and one of the most studied subjects in Biology, including a fully sequence of its genome, a well-understood life cycle and its ecology. Daphniids are keystone organisms for environmental toxicity studies because they are considered as primary consumer in aquatic food chains. [A. Siciliano, R. Gesuele, G. Pagano, M. Guida, How *Daphnia* (cladocera) assays may be used as bioindicators of health effects? *J. Biodivers Endanger Species*, 1, 5 (2015)]

Why *Daphnia*? In our study, we chose *Daphnia* because they are filter feeders that conduct small suspended particles into their mouth by the current created by the motion of their leaf-like legs, which makes *Daphnia* an ideal candidate for our toxicity study of BNNTs and dyes@BNNTs suspended in a culture medium (FLAMES/Spring water). Furthermore, in optimal environmental conditions, daphniids reproduce by cyclical parthenogenesis, by generation of diploid eggs that develop directly into larvae at the female brood chamber. The parthenogenesis entails clonal reproduction. The sexual reproduction of daphniids is trigged by environmental stress (e.g. crowding, cooling, changes of photoperiod), which was avoided in our study. Moreover, we used only individuals that did not carry eggs or resting eggs or any larvae in the brood chamber. The maximum incubation time of daphniids with our samples (BNNTs, DPPx@BNNTs, 6T@BNNTs) was 12 hours, which is not enough to affect the reproduction cycle, which is 3 days. *Daphnia* is an ideal system to study of PL from dyes@BNNTs because of its feeding and reproduction systems, which allows us to have identical individuals in the laboratory.

Dyes@BNNT in Daphniids Experiments:

A) Preparation of 6T, 6T@BNNT, DPPx@BNNT and BNNT:

The samples for *Daphnia* with Dye@BNNT and BNNT were prepared from a stock solution (1 mg/ml) by dispersion in FLAMES culture media at an appropriate concentration, typically between 5 and 100 µg/ml.

For each incubation experiment, about 5 *Daphnia* were carefully transferred to the prepared Spring water/dyes@BNNT solution and incubated for the required time. After the incubation, one drop of the solution containing a *Daphnia* was transferred to a glass slide using a drop of its incubation medium. The area is approximately the size of the field of view of our 4× objective.

B) Incubation of 6T, 6T@BNNT and DPPx@BNNT with *Daphnia pulex:*

Before any experiment, many adult individuals of *Daphnia pulex* (clones DISP 1312) were kept at 22° C. in FLAMES with algae for 4 days, allowing a new reproducing cycle. Then, the specimens were transferred to a FLAMES medium algae-free and maintained this condition for at least 1 day to clean the digestive system and limit the fluorescence from the algae themselves during the images/time lapse acquisition—FIG. 8.

The daphniids were divided into 2 control groups, and 5 additional groups labelled 6T@BNNT, DPP2@BNNT, DPP3@BNNT, BNNT and 6T, as described in the Table S1 below. Daphniids were transferred to 6 vials according to Table S1.

TABLE S1

Description of the groups of daphniids created for this study by type of sample used for the incubation

| Group of daphnia | Description of the group |
|---|---|
| A | Daphniids incubated with BNNTs dispersed into algae-free FLAMES (50 µg/mL) |
| B | Daphniids incubated with 6T dispersed into algae-free FLAMES (µg/mL) |
| C | Daphniids incubated with 6T@BNNT dispersed into algae-free FLAMES (5 µg/mL) |
| D | Daphniids incubated with DPP2@BNNT dispersed into algae-free FLAMES (5 or 50 µg/mL) |
| E | Daphniids incubated with DPP3@BNNT dispersed into algae-free FLAMES (5 µg/mL) |
| Control 1 | Daphniids kept into algae-free FLAMES which were used to observe any inherent photoluminescence of the *Daphnia pulex* at the conditions of our study. |
| Control 2 | Daphniids kept into algae-free FLAMES to observe the maximum period which the individuals would resist before death by starvation |

C) PL Measurements of 6T, 6T@BNNT, DPPx@BNNT and BNNT with *Daphnia pulex*:

To perform the PL measurements, each *Daphnia* was transferred with the incubation medium to a glass slide. The excess of liquid was dried out in order to keep the minimum necessary to maintain the *Daphnia* alive. Following this step, movies of the PL from dyes@BNNTs in the *Daphnia* were acquired using a UBG filter. Further, PL measurements related to the interval of t=0 to t=12 hours had a duplicate slide for which the liquid was dried out. The daphniid used was kept in air.

The NIR PL image at 900 nm in FIG. 4D (main text) was performed using a *Daphnia pulex* individual incubated with DPP3@BNNT (5 µg/mL) and recorded using an Hyperspectral Raman/PL Imager—RIMA™ (Photon etc, laser power of 500 mW, 10× objective, acquisition time 2 sec)

D) Evaluation of Potential Toxicity and Reverse Cycle of Incubation of *Daphnia* with 6T@BNNT, DPP3@BNNT and BNNT:

In order to evaluate the potential toxicity of our samples (6T, 6T@BNNT, DPPX@BNNT and BNNT), we kept 3 individuals of each group (Table S1) to evaluate potential death by contact with our samples. The *Daphnia* were incubated for a period of 36 hours and there was no observed death of individuals, except from group B (incubated directly with 6T at 100 ug/mL) who died after 20 hours. To evaluate the capacity of the daphniids to get rid of the 6T@BNNT, DPP3@BNNT and BNNT after the experiments, we transferred individuals of groups A, C, D and of Control 1 to an algae-free FLAMES (for 2 hours) followed by FLAMES/algae medium. All the individuals survived after the experiments. Further, they were monitored for more than 30 days after full cycle of reproduction.

2.10 Photobleaching experiments on Dye@BNNT assemblies. The stability of the dye@BNNT was assessed in solution and compared to the dye alone, after exposition overnight to a conventional lamp—FIG. 10.

2.11 Preparation of hepatoblastoma HuH6 cells. HuH6 cells were grown in DMEM under low glucose conditions (PanBiotech, P04-01550), supplemented with 10% calf serum (Dutscher, S1810) and 1% penicillin/streptomycin mixture (PanBiotech, P06-07050) in T75 flasks and passaged when reach 75% confluency.

2.12 6T@BNNT Experiments with Human Hepatoblastoma HuH6 Cells i) Preparation of the solution of PEG-6T@BNNT and PEG-DPP3@BNNT for the tracking experiments presented in FIG. 5e (main text). Purified BNNTs were centrifuged at 10k rpm (12 350 g) for 1 h. The encapsulation was done in a 6T solution (C=5×10$^{-5}$ M) for 24h at 120° C., followed by extensive washing and vacuum filtration until the filtrate was colourless. The collected sample was washed in water several times, then in a solution of mPEG-DSPE at 200 µM, for a final concentration of 50 µg/mL of 6T@BNNT in the PEG solution.

ii) Preparation of the solution used for the toxicity study and the bleaching tests presented in FIGS. 5a and 5b, respectively. The encapsulation of 6T@BNNT was done in the same manner as described above. The 6T@BNNT sample was solubilized in two mPEG-DSPE concentration (400 µM and 20 µM), for a final concentration of 100 µg/mL of 6T@BNNT in both cases.

iii) Incubation of HuH6 cells with PEG-6T@BNNT. Incubation for the hyperspectral luminescence imaging (FIG. 5a, main text): 100 µL of the solution described in ii) above was added to 1 mL of DMEM and injected in two different wells containing the cells and incubated for 24 hours before rinsing with DMEM. Before imaging, the cells membranes of the well #1 are revealed using 5 µL·mL$^{-1}$ of Fast DiA fluorophore during 10 mins while the cells in the well #2 were exposed to green Calcein during 30 mins at 6 µM (equivalent to 6.25 µg·mL-1) for positive staining of the living cells.

Incubation for the two-photon imaging (FIG. 5b, main text): 100 µL of the solution described in ii) was added to 1 mL of DMEM and injected in the well containing the cells and incubated for 24 hours before rinsing with DMEM. Then the cells were fixed overnight using PFA 4% at 4° C. Before imaging, the cells membranes were revealed using 5 µL·mL$^{-1}$ of Fast DiA fluorophore for 10 mins.

Incubation for the nanoprobes tracking experiment (FIG. 5e, main text): 100 µL of the solution described in i) was added to 1 mL of DMEM and injected in the well containing the cells, during 24 hours, before rinsing with DMEM.

3) Characterization 3.1 Characterization by AFM. The AFM images were produced using a Dimension 3100 scanning probe microscope equipped with a Nanoscope IV controller and a quadrex extender module. Height images were acquired using silicon probes in intermittent-contact mode with a nominal spring constants of 42 Nm$^{-1}$, resonance frequency of ~320 Hz, and tip radius curvature<10 nm.

3.2 Characterization by Raman and Photoluminescence.

The Raman/PL measurements were taken from different setups depending on the experiment. The equipment of the 5 different setups is summarized in Table S2 and are described as follows:

The Luminescence images and photobleaching experiments, as presented in FIG. 3, main text, were performed at $\lambda_{ex}$=532 nm using the Raman/PL mapping system RIMA™ (Photon etc.). For luminescence mode imaging, the signal is the integrated intensity of the fluorescence using a 100× objective and a laser power ranging from 0.5 µW·µm$^{-2}$ to 80 µW·µm$^{-2}$.

The PL spectra in FIG. 3D (main text) were acquired on a Raman/PL Renishaw Spectrometer.

The optical image of the *Daphnia pulex* presented in the panel #1 in FIG. 4 (main text) was done using a conventional confocal microscope. A z-stack of 20 images was acquired to probe the volume of the *Daphnia* and then the Auto-blend function in Phostoshop was applied to reconstruct the image.

The fluorescence images in FIG. 4 (main text) were acquired with an Olympus confocal microscope equipped with a U-RFL-T mercury light source, a BX-UCB controller and a DP71 digital camera. The images were acquired with a 10× objective and UBG, TRITC and TXRED filters. The acquiring conditions were: Exposure time: ½₀ sec; ISO sensitivity: ISO 200.

The hyperspectral fluorescence images presented in FIGS. 5a and 5e (main text) were acquired with a Leica microscope SP8 WLL2 on an inverted stand DMI6000 (Leica Microsystems, Mannheim, Germany) using a HCX Plan Apo CS2 63× oil NA 1.40 objective (FIG. 5a, main text) or a HC PL FLUOTAR 10×/0.30 DRY objective (FIG. 5e—time lapse, main text). The spectral interval of the collection channels C1 and C2 are: 490-520 nm and 600-780 nm, respectively.

The photobleaching test consisted in a continuous scanning in two-photon conditions, i.e. 400 Hz at an excitation wavelength of 860 nm during 30 mins. The laser output power is 2.55 W The hyperspectral two-photon fluorescence images and the excitation profile presented in FIGS. 5b and 5d (main text) were acquired on a Leica TCS SP5 on an upright stand DM6000 (Leica Microsystems, Mannheim, Germany) using either Argon laser or Mai Tai HP laser (SpectraPhysics, Irvine, USA) and a HC PL APO CS2 40.0×1.30 OIL objective. The conditions are as follows:

The excitation profile presented in FIG. 5d (main text) was extracted from a x/y/$\lambda_{ex}$ fluorescence datacube with 740<$\lambda_{ex}$<1020 and $\Delta\lambda_{ex}$=20 nm. The photobleaching test consisted in illuminating a defined area with two-photon imaging condition during 30 min (400 Hz, laser output power of 2.55 W, 40× NA1.3 objective).

A luminescence xyz datacube was then recorded ($\Delta z$=0.7 µm) from the collection channels C1 and C2. The spectral interval of C1 and C2 are 500-530 nm and 645-715 nm, respectively. We applied a z-projection of 5 consecutive images of the Z-stack centred at the deepness of the photo-bleaching focus. A Kalman filter was finally used to present FIG. 5b (main text).

The time-lapse imaging datacube for the tracking experiments is formed by images acquired every 650 ms using two channels, one for the DiA (C1) and one for the PEG-6T@BNNT (C2). A post treatment was applied as follows: 1: subsampling to obtain an image every 9.75 sec; 2: C2-C1 operation; 3: Kalman filter; 4: median filter with kernel 1. We used the tracking algorithm TrackMate to determine the successive positions of the nanoprobes. The reconstructed trajectories were finally merged with C1 to produce the image in FIG. 5e bottom (main text). To be able to distinguish isolated positions of the nanoprobe in FIG. 5e (top) in the main text, the image was constructed by superposing sequential images extracted every 9.75 sec from the treated datacube.

TABLE S2

Raman/Absorption/Photoluminescence setups used for the experiments

| Set up | Excitation | Objective | Dispersive element | Detection |
| --- | --- | --- | --- | --- |
| Horiba JY Spectrofluorometer for solutions (FIG. 1b) | 450 W Xe lamp Coupled to double monochromator | | iHR320 monochromator with 1800 and 150 tt/mm gratings | LN2 cooled InGaAs array (NIR) and R928 PMT (Vis) |
| Brucker Vertex 80v Absorption spectrometer (FIG. 1b) | Tungsten lamp | | CaF2-T602 Beamsplitter | GaP-D520 and Si-D510 detectors |
| Custom optical bench (FIG. 4c) | Verdi 532 nm HeNe 633 nm | Olympus 50X long working distance NA 0.55 | Grating, 600 and 1800 tt/mm | CCD JY nitrogen cooled |
| Photon etc. RIMA imager system (FIG. 3 and 4d) | Opus 532 nm | Olympus 100X | no (broadband mode) optical filters | CCD Pixis (Princeton Inst.) Peltier |
| Renishaw InVia Reflex (FIG. 3d) | Cobolt 473 nm | Olympus 50X | Grating, 1200 and 2400 tt/mm | CCD Renishaw RemCam, Peltier |
| Fluorescence microscope (FIG. 4) | U-RFL-T mercury light source | 10X | no | UBG, TRITC and TXRED filters |
| Fluorescence microscope Leica SP8 WLL2 | Argon laser | HCX Plan Apo CS2 63X oil NA 1.40 objective or | | |

TABLE S2-continued

Raman/Absorption/Photoluminescence setups used for the experiments

| Set up | Excitation | Objective | Dispersive element | Detection |
|---|---|---|---|---|
| (FIG. 5a) | | HC PL FLUOTAR 10x/0.30 DRY objective | | |
| Tw-photo fluorescence microscope Leica TCS SP5 (FIG. 5b) | Argon laser or Mai Tai HP Ti-Sapph laser | HC PL APO CS2 40.0 × 1.30 OIL | | |

Figure 10:
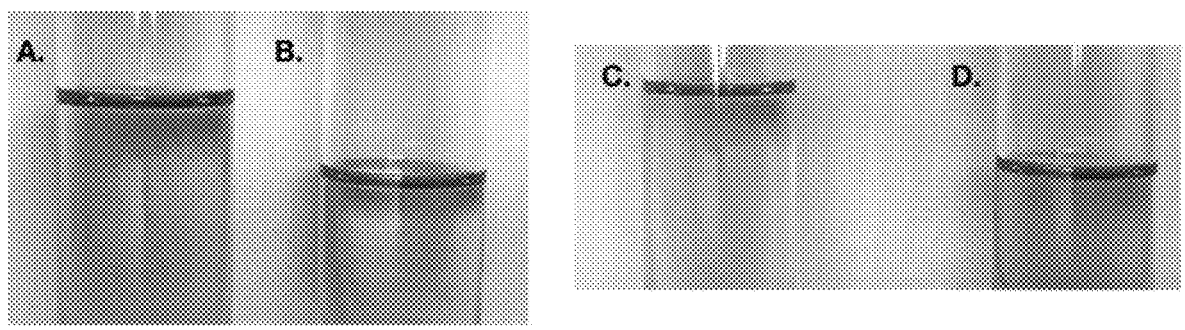
FIG. 10. A) DPP2 in DMF; B) DPP2@BNNT in DMF; C) DPP2 in DMF after light exposition overnight; D) DPP2@BNNTs in DMF after overnight light exposition. Slight changes in lighting conditions accounts for the colour difference seen here for the DPP2@BNNT solution.
Figure 11:
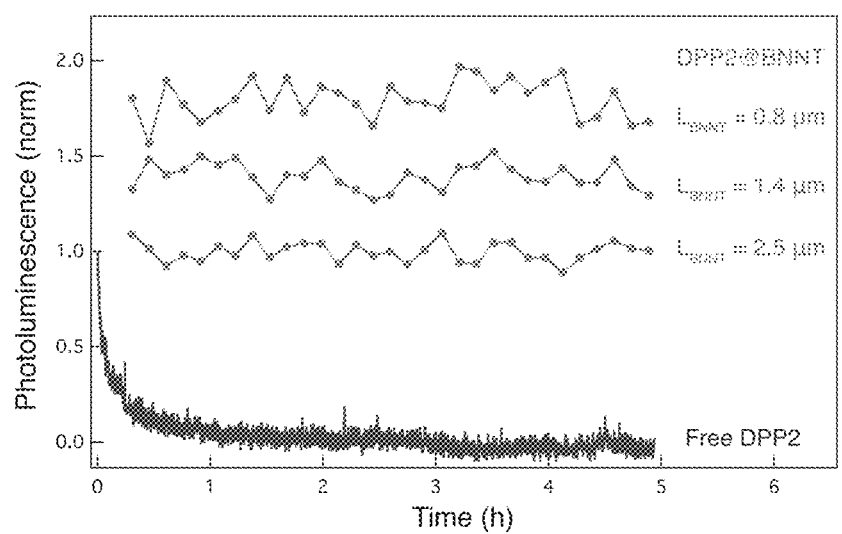
FIG. 11. Photoluminescence of isolated DPP2@BNNT deposited on a Si/SiO2 substrate as a function of time and compared to free DPP2 molecules deposited on the same substrate. The excitation wavelength is 532 nm and the laser fluence is 1.2 µW·µm$^{-2}$.

3.3 Characterization by HR-TEM and TEM-EELS. TEM and high-angle annular dark-field (HAADF) STEM images in FIG. 1 (main text) and FIG. 7(*a-b*) were recorded with a Libra 200 MC Zeiss operating at 200 kV and at 80 kV. The microscope is equipped with a monochromatic Schottky FEG source delivering an energy resolution of about 150 meV and a Gatan Ultrascan camera. Point resolution is 2.3 Å and information limit is 1.2 Å at 200 kV. The TEM can operate in scanning mode (STEM) and is equipped with Bright Field (BF) and HAADF detectors. An in-column energy filter makes possible energy filtered TEM (EFTEM) imaging, EELS measurements in Scanning mode and the acquisition of spectral image datacubes (or hyperspectral EELS). The STEM-HAADF probe size is about 2.5 nm (FIG. 10).

Figure 12:
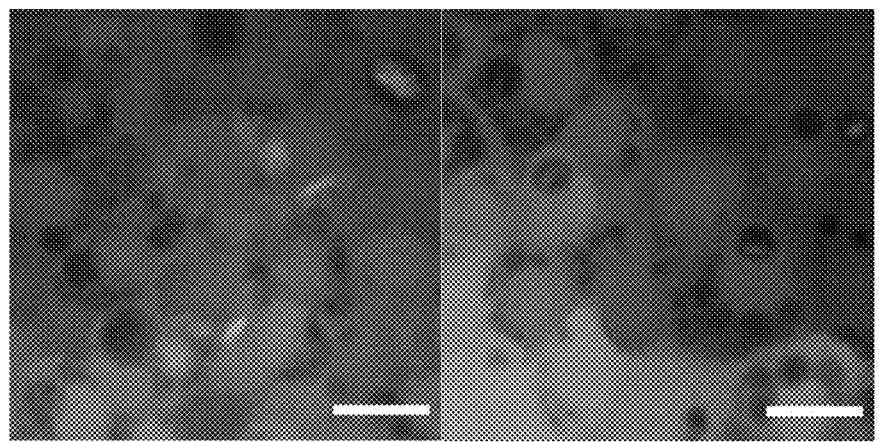
FIG. 12 Typical hyperspectral images of HuH6 cells incubated 24 hours with PEG-6T@BNNT (red) and then exposed to Calcein (green) for 30 mins at a concentration of 6.25 µg·mL$^{-1}$ for lethality assessment. The scale bar is 20 µm

The high-resolution images presented in FIG. 1F (main text) and FIG. 12 below were performed at 80 kV on a JEOL ARM microscope, equipped with an aberration corrector.

The invention claimed is:

1. A fluorescent probe comprising a capsule of nanometric size, the capsule being a boron nitride nanotube, the fluorescent probe further comprising an aggregate of fluorogenic molecules coupled to the capsule, the aggregate emitting a fluorescent signal at one or more wavelengths within a near-infrared fluorescence spectral range when the probe is illuminated by an excitation light beam at one or more wavelengths within a visible or NIR1 excitation spectral range.

2. The fluorescent probe according to claim 1, wherein the aggregate comprise 3,6-Bis[2,2']bithiophenyl-5-yl-2,5-di-n-octylpyrrolo[3,4-c]pyrrole-1,4-dione as fluorogenic molecules.

3. The fluorescent probe according to claim 1, wherein the fluorogenic molecules are in a J-aggregation state.

4. The fluorescent probe according to claim 1, wherein the fluorogenic molecules are in a combination of a J-aggregation state and a H-aggregation state.

5. The fluorescent probe according to claim 1, wherein the fluorescent spectral range of the aggregate of fluorogenic molecules is shifted with respect to a fluorescent emission spectrum of said fluorogenic molecules in a free state by a spectral shift of the order of 600 nm.

6. The fluorescent probe according to claim 1, wherein the fluorescent spectral range of the aggregate of fluorogenic molecules is broadened with respect to a fluorescent emission spectrum of said fluorogenic molecules in a free state.

7. The fluorescent probe according to claim 1, wherein the fluorescent signal comprises multiple peaks in the NIR2 range upon excitation by the excitation light beam at a wavelength in the NIR1 range.

8. A fluorescent probe, comprising a capsule of nanometric size and an aggregate of fluorogenic molecules coupled to the capsule, the aggregate emitting a fluorescent signal at one or more wavelengths within a near-infrared fluorescence spectral range when the probe is illuminated by an excitation light beam at one or more wavelengths within a visible or NIR1 excitation spectral range, the aggregate comprising 3,6-Bis[2,2']bithiophenyl-5-yl-2,5-di-n-octylpyrrolo[3,4-c] pyrrole-1,4-dione as fluorogenic molecules.

9. The fluorescent probe according to claim 8, wherein the fluorogenic molecules are in a J-aggregation state.

10. The fluorescent probe according to claim 8, wherein the fluorogenic molecules are in a combination of a J-aggregation state and a H-aggregation state.

11. The fluorescent probe according to claim 8, wherein the fluorescent spectral range of the aggregate of fluorogenic molecules is shifted with respect to a fluorescent emission spectrum of said fluorogenic molecules in a free state by a spectral shift of the order of 600 nm.

12. The fluorescent probe according to claim 8, wherein the fluorescent spectral range of the aggregate of fluorogenic molecules is broadened with respect to a fluorescent emission spectrum of said fluorogenic molecules in a free state.

13. The fluorescent probe according to claim 8, wherein the fluorescent signal comprises multiple peaks in the NIR2 range upon excitation by the excitation light beam at a wavelength in the NIR1 range.

14. A fluorescent probe, comprising a capsule of nanometric size and an aggregate of fluorogenic molecules coupled to the capsule, the fluorogenic molecules being in a combination of a J-aggregation state and a H-aggregation state the aggregate emitting a fluorescent signal at one or more wavelengths within a near-infrared fluorescence spectral range when the probe is illuminated by an excitation light beam at one or more wavelengths within a visible or NIR1 excitation spectral range.

15. The fluorescent probe according to claim 14, wherein:
the capsule is a boron nitride nanotube; and
the aggregate comprise 3,6-Bis[2,2']bithiophenyl-5-yl-2, 5-di-n-octylpyrrolo[3,4-c]pyrrole-1,4-dione as fluorogenic molecules.

16. The fluorescent probe according to claim 14, wherein the fluorescent spectral range of the aggregate of fluorogenic molecules is shifted with respect to a fluorescent emission spectrum of said fluorogenic molecules in a free state by a spectral shift of the order of 600 nm.

17. The fluorescent probe according to claim 14, wherein the fluorescent spectral range of the aggregate of fluorogenic molecules is broadened with respect to a fluorescent emission spectrum of said fluorogenic molecules in a free state.

18. The fluorescent probe according to claim 14, wherein the fluorescent signal comprises multiple peaks in the NIR2 range upon excitation by the excitation light beam at a wavelength in the NIR1 range.

* * * * *